United States Patent
Levin et al.

(10) Patent No.: US 12,029,411 B2
(45) Date of Patent: Jul. 9, 2024

(54) SURGICAL FASTENING DEVICE

(71) Applicant: CATCHER TECHNOLOGY CO., LTD., Tainan (TW)

(72) Inventors: Ofek Levin, Moshav Amirim (IL); Arie Levy, Shoham (IL); Lena Levin, Moshav Amirim (IL)

(73) Assignee: CATCHER TECHNOLOGY., LTD., Tainan (TW)

( * ) Notice: Subject to any disclaimer, the term of this patent is extended or adjusted under 35 U.S.C. 154(b) by 551 days.

(21) Appl. No.: 17/420,693

(22) PCT Filed: Jan. 3, 2020

(86) PCT No.: PCT/IB2020/000017
§ 371 (c)(1),
(2) Date: Jul. 5, 2021

(87) PCT Pub. No.: WO2020/141458
PCT Pub. Date: Jul. 9, 2020

(65) Prior Publication Data
US 2022/0096075 A1  Mar. 31, 2022

Related U.S. Application Data

(60) Provisional application No. 62/788,359, filed on Jan. 4, 2019.

(51) Int. Cl.
*A61B 17/04* (2006.01)
*A61B 17/06* (2006.01)

(52) U.S. Cl.
CPC ...... *A61B 17/0469* (2013.01); *A61B 17/0487* (2013.01); *A61B 17/06166* (2013.01);
(Continued)

(58) Field of Classification Search
CPC ............ A61B 17/0469; A61B 17/0487; A61B 17/06166; A61B 17/0644; A61B 17/068;
(Continued)

(56) References Cited

U.S. PATENT DOCUMENTS 5,582,616 A  12/1996  Bolduc et al.
8,535,339 B2  9/2013  Levin et al.
(Continued)

FOREIGN PATENT DOCUMENTS

WO  2017/163119 A1  9/2017
WO  WO-2017163119 A1 *  9/2017  ......... A61B 17/0644

OTHER PUBLICATIONS

International Search Report and Written Opinion issued in International Application No. PCT/IB2020/00017, dated Jul. 28, 2020, 9 pages.
(Continued)

*Primary Examiner* — Jocelin C Tanner

(57) ABSTRACT

Devices and methods for delivering surgical fasteners to a controlled, specific depth in tissue and locking the fasteners closed to provide a secure and reliable attachment. Devices includes a body with a handle with a trigger extending therefrom; a shaft extending from the body; a delivery tip at a distal end of the shaft; a driver member disposed within the shaft; and a fastener with no points, barbs, or sharp edges held at the delivery tip. The fastener is inserted into a fixed depth and locks into a closed loop.

20 Claims, 26 Drawing Sheets

(52) U.S. Cl.
CPC .............. *A61B 2017/0488* (2013.01); *A61B 2017/06176* (2013.01)

(58) Field of Classification Search
CPC .......... A61B 17/42; A61B 2017/00867; A61B 2017/06176; A61B 2017/0647
See application file for complete search history.

(56) References Cited

U.S. PATENT DOCUMENTS

| | | | |
|---|---|---|---|
| 8,789,736 B2 | 7/2014 | Dudai | |
| 2013/0158567 A1* | 6/2013 | Levin | A61B 17/0469 606/144 |
| 2014/0330292 A1 | 11/2014 | Levin et al. | |
| 2016/0310146 A1* | 10/2016 | Levy | A61B 17/0485 |

OTHER PUBLICATIONS

Oliphant, 2010, Trends over time with commonly performed obstetric and gynecologic inpatient procedures, Obstet Gynecol, 116(4):926-931.

* cited by examiner

Normal uterus

Prolapsed uterus

SURGICAL FASTENING DEVICE

CROSS-REFERENCE TO RELATED APPLICATION(S)

This application is a National Phase of PCT Patent Application No. PCT/IB2020/000017 having International filing date of Jan. 3, 2020, which claims the benefit of priority under 35 USC § 119(e) of U.S. Provisional Application No. 62/788,359, filed on Jan. 4, 2019. The contents of the above applications are all incorporated by reference as if fully set forth herein in their entirety.

TECHNICAL FIELD

Surgical fastening devices, surgical fasteners, and surgical methods.

BACKGROUND

Prolapse is a medical condition in which organs, such as the uterus, fall down or slip out of place. For example, pelvic organ prolapse involves a loosening of connective tissue that holds the uterus, allowing the uterus to descend into the vagina. It is estimated that half of all women older than 50 years may experience symptomatic prolapse. The health care impact of prolapse is likely to expand, based on an aging population. Surgical repair of prolapse has been one of the most common procedures performed in women over 70.

Laparoscopic sacrocolpopexy is a surgical technique for repairing pelvic organ prolapse in which a piece of a pre-shaped mesh is inserted into the abdomen and attached at one end to the vaginal tissue and at the other end to the back portion of the sacral promontory, thereby lifting the vagina and preventing the prolapse. Attachment of the mesh to the vagina wall by suturing is challenging because it requires the insertion of the suture to a specific depth into the vaginal wall. The suture must provide a secure attachment, but should not pass through the vagina wall since that could cause serious complications.

SUMMARY

The invention provides devices and methods for delivering surgical fasteners to a controlled, specific depth in tissue and locking the fasteners closed to provide a secure and reliable attachment. Fasteners of the present invention do not have barbs, points, or similar traumatic edges or features; instead, delivery devices are provided that provide the piercing functionality to deliver the atraumatic fastener into tissue. Devices and fasteners of the invention may be used to secure a mesh to tissue, and thus may be used in sacrocolpopexy procedures to treat prolapse conditions such as pelvic organ prolapse. The surgical fastening device will automatically apply individual fasteners through the mesh and into the vaginal wall. The suture is inserted into a fixed depth, minimizing risk of piercing through the vagina wall and providing a reliable attachment. Because the device locks the individual fasteners into closed loops, there is no need for knot tying and thus devices and methods of this disclosure reduce the time and skill required to perform such a procedure. Because the procedure can be performed more readily and quickly than by other methods, the procedure will be less expensive and thus more widely available. Device of the invention will allow a greater number of people to be treated to alleviate suffering from prolapse conditions.

Surgical fastening devices and fasteners described herein provide benefits and advantages for surgical procedures such as laparoscopic sacrocolpopexy for pelvic organ prolapse (POP). For example, because a fastener can be wider than a shaft diameter, the fastener is not limited in the width to the 5 mm diameter of a laparoscopic instrument. Even for fasteners that will penetrate only to a shallow depth, they can be wide (e.g., wider than the penetration depth). The generous width contributes to reliably securing a mesh to tissue.

Additionally, devices have a tip that is angled in relation to the tissue or the shaft of the device. This means that the device shaft need not point straight towards the target tissue surface and a fastener can be deployed somewhat towards the side of the tip of the shaft. This may be prove convenient in many procedures.

Devices may be used to apply fasteners into only a very small depth, which is important for several applications. Because the device contains a driver member that extends from a tissue-facing surface at an acute angle and curves back to the tissue facing surface, the penetration depth can be very shallow. The acute angle may preferably be between 5° and 60°. The closed loop of the fastener can span a width across the tissue that is wide and therefore strong. In fact, the width can be wider than a diameter of the shaft of the device. The very shallow penetration depth is important in applications such as laparoscopic sacrocolpopexy is which the fastener must provide a secure attachment without passing through the vagina wall.

Additionally, the fasteners disclosed herein have no sharp edges pointing into the tissue. Such sharp edges may otherwise irritate the nerves and tissue. The disclosed fasteners, when closed, contain all points or barbs within a smooth bowl of material and present only smooth surfaces to the surrounding tissue.

The surgical fastening device includes a driver member that extends from a tissue-facing surface at an acute angle and curves back to the tissue facing surface. The driver member is made of a super-elastic material such as Nitinol. Such a material is advantageous because it gives the driver member the strength and shape necessary to allow it to fasten the fastener in the shallow, broad, edge-free configuration useful and beneficial for procedure such as laparoscopic sacrocolpopexy.

Aspects of the disclosure provide a surgical fastening device that includes: a shaft comprising a proximal portion and a distal end; a positionable delivery tip at the distal end of the shaft, the delivery tip positionable in a first position substantially extending along an axis of the shaft and a second position angled away from the axis of the shaft; a driver member disposed within the shaft; and a fastener held at the delivery tip, the fastener having an extended body with a receiving end and an opposite end, wherein the driver member is operable to: push the receiving end of the fastener out of the delivery tip, along a path back toward a distal end of delivery tip, push the opposite end towards the distal end of the delivery tip to the receiving end to form the fastener into a closed fastener, and release from the closed fastener. The device may include a body connected to the proximal portion of the shaft, the comprising a handle and having a trigger extending therefrom. Preferably operation of the trigger causes the driver member to retract back into the shaft and engage a second fastener after the closed fastener is released. The device may include at least one internal driver member adapted to push said opposite end along the delivery tip to the distal end thereof once said receiving end is back in the delivery tip. Preferably the delivery tip is rotatable, relative to the shaft, between the first position and the second position. Optionally the delivery tip is in said first position when external constraining forces are applied thereon. In some embodiments when said device is in a trocar the delivery tip is in said first position and when said device exits said trocar the delivery tip assumes the second position. Preferably the delivery tip protrudes from the shaft and presents a tissue-facing surface with an exit port thereon. The fastener may be held at the delivery tip at least partially within a guide slot. The delivery tip is preferably biased away from the shaft such that, when in the second position, the axis of the shaft and the tissue-facing surface form an acute angle. The driver member may include a shape-memory material that biases the driver member into a curved shape. Optionally the driver member is disposed within the shaft, the driver pushing member is constrained by the shaft into a straight shape. In certain embodiments the driver member comprises at least one sharp tip adapted to penetrate a tissue. The driver member may additionally comprise at least one hook adapted to engage with the receiving end of said fastener. In certain embodiments, the opposite end of the fastener comprises no barbs or sharp edges and the receiving end is shaped as a loop. In some embodiments, the shaft has a length L of at least 15 cm and has a diameter D of less than 1.55 cm. Preferably the delivery tip, when unconstrained, assumes the second position and is bendable towards the axis of the shaft. Most preferably the device includes a plurality of additional fasteners disposed with the shaft, wherein each operation of the trigger delivers a single fastener and advances the additional fasteners towards the delivery tip. Preferably the fastener is formed into the closed fastener through the driver member solely with no other member extending from the delivery tip. The device may include at least one internal driver member operable to push the opposite end of said fastener through the delivery tip and into position to engage with the receiving end of said fastener to form a closed fastener.

Certain aspects of the disclosure provide a surgical fastening device that includes an extended shaft comprising a proximal portion and a distal end; a delivery tip at a distal end of the shaft, the delivery tip protruding from the shaft and presenting a tissue-facing surface with an exit port thereon, wherein the delivery tip is biased away from the shaft such that an axis of the shaft and the tissue-facing surface form an acute angle, wherein the delivery tip is bendable towards the axis of the shaft, and wherein the exit port a distal end of a delivery slot extending through the shaft; a driver member disposed within the shaft; and at least one fastener held at the delivery tip at least partially within a guide slot in spatial communication with the exit port, the fastener having an extended body with a opposite end and a receiving end, wherein the opposite end comprises at least one engagement feature and a pushable surface engaged with a distal tip of the pushing member, and wherein the receiving end defines a bowl with an opening and a lip that overhangs the opening, and in which operation of the trigger causes the driver member to: push the receiving end of the fastener out of the delivery tip, along a path back toward the delivery tip, the opposite end is pushed towards the distal end of the delivery tip into the receiving end of the fastener, thereby forming the fastener into a closed fastener, release from the closed fastener. The device may include a body with a handle extending therefrom attached to the proximal portion of the shaft; and a trigger on the handle. In some embodiments the engagement feature of the opposite end is captured by the bowl to form the fastener into the closed fastener. Preferably operation of the trigger causes the driver member to retract back into the shaft and engage a second fastener after the closed fastener is released. Most preferably the delivery tip is deformable into an straight position extending substantially along an axis of the shaft, and can be held in the straight position by a trocar during passage through the trocar. In some embodiments the driver member comprises a shape-memory material that biases the driver member into a curved shape. The driver member may be disposed within the shaft, the driver pushing member is constrained by the shaft into a straight shape. The engagement feature at the opposite end of the fastener may present no barbs or sharp edges. In some embodiments the shaft has a length L of at least 15 cm and has a diameter D of less than 1.55 cm. Preferably the distal end of the shaft fits through a trocar with diameter of less than about 1.5 cm when the deliver tip is bent towards the axis of the shaft. Preferably the shaft carries a plurality of fasteners, and when the device delivers the fastener, the driver member engages a next one of the plurality of fasteners and moves the next one of the plurality of fasteners into the delivery tip.

Other aspects of the disclosure provide a surgical fastening device comprising: an extended shaft dimensioned for insertion into a surgical site; a delivery tip at the distal end of the shaft, wherein the delivery tip is naturally rests at a default configuration angled away from an axis of the shaft and is conformable to a second configuration aligned with said shaft; a driver member disposed within the shaft; and a fastener held at the delivery tip, the fastener having an extended body with a receiving end and an engaging end, wherein the device is operable to push, via the driver member, the receiving end of the fastener out of the delivery tip, along a path back toward the distal end of delivery tip, push the engaging end towards the distal end of the delivery tip into the receiving end to form the fastener into a closed fastener, and release from the closed fastener. Preferably the engaging end does not have any points or barbs. In some embodiments, the receiving end comprises an open loop and the engaging end comprises a wide portion that gets captured by the open loop when the engaging end is pushed into the receiving end. The device may include a body comprising a handle and having a trigger extending therefrom, wherein the extended shaft extends from the body. Operation of the trigger may cause the driver member to retract back into the shaft and engage a second fastener after the closed fastener is released. Preferably when said device is in a trocar the delivery tip is in said second configuration and when said device exits said trocar the delivery tip assumes the default configuration. In some embodiments, placing the tissue-facing surface against tissue and operating the device causes the driver member to push the receiving end through the tissue and to the engaging end of the fastener outside of the tissue such that the closed fastener spans a width W across a surface of the tissue and penetrates to a depth H within the tissue. E.g., the shaft may have a length L of at least 15 cm and a diameter D of less than 1.55 cm (e.g., L≥25 cm and D≤10 mm, more preferably H<D<W). Optionally, the driver member comprises at least one sharp tip adapted to penetrate the tissue. The driver member additionally may comprise at least one hook adapted to engage with the receiving end of said fastener, the hook adapted to grasp the receiving end of said fastener, wherein the receiving end of said fastener is enclosed by said hook and said sharp tip of the driver member.

In certain aspects, the invention provides a surgical fastening device. The device includes a body with a handle with a trigger extending therefrom; a shaft extending from the body; a delivery tip at a distal end of the shaft; a driver member disposed within the shaft; and a fastener held at the delivery tip. The fastener has an extended body with a barbed end and a receiving end. Operation of the trigger causes the driver member to: push the barbed end of the fastener out of a tissue-facing surface of the delivery tip, along a curved path and back to the tissue-facing surface, and into the receiving end, thereby forming the fastener into a closed fastener; release from the closed fastener; and retract back into the shaft and engage a second fastener. Preferably, only a single driver member extends from the delivery tip to fasten the fastener. The delivery tip may protrude from the shaft and present a tissue-facing surface with an exit port thereon. The fastener is held at the delivery tip at least partially within a guide slot in spatial communication with the exit port. Preferably, the delivery tip is biased away from the shaft such that an axis of the shaft and the tissue-facing surface form an acute angle, The driver member comprises a shape-memory material that biases the driver member into a curved shape. When the driver member is disposed within the shaft, the driver member is constrained by the shaft into a straight shape. In some embodiments, the barbed end of the fastener includes one or more barbs and a pushable surface engaged with a distal tip of the driver member, e.g., disposed within a delivery slot that terminates at the exit port. The receiving end of the fastener may define a bowl with an opening and a lip that overhangs the opening. The receiving end may be positioned for delivery within a distal end of the guide slot within the delivery tip. In certain embodiments, the exit port encompasses the distal end of the delivery slot and is in spatial communication with a distal end of the guide slot.

Operation of the trigger causes the driver member to: push the barbed end of the fastener out of the distal end of the delivery slot, along a curved path to the distal end of the guide slot, and into the receiving end of the fastener such that the one or more barbs are engaged with the lip of the bowl of receiving end, thereby forming the fastener into a closed fastener. Preferably, placing the tissue-facing surface against tissue and pulling the trigger causes the driver member to push the barbed end through the tissue and into the receiving end of the fastener outside of the tissue such that the closed fastener spans a width W across a surface of the tissue and penetrates to a depth H within the tissue. The shaft may have a length L of at least 15 cm and has a diameter D of less than 1 cm. In certain embodiments, L≥25 cm and D≤7 mm and H<D<W.

The delivery tip may be bendable towards the axis of the shaft.

The device may include additional fasteners disposed with the shaft, wherein each operation of the trigger delivers a single fastener and advances the additional fasteners towards the delivery tip.

Aspects of the invention provide a surgical fastener that includes an extended body, at least a portion of the extended body being flexibly deformable, the extended body terminating at an engaging end and a receiving end, wherein the receiving end defines a loop with an opening. The engaging end does not include any point or barb. Bending the deformable portion of the extended body and inserting the engaging end into the receiving end locks the fastener in a closed loop. Preferably, the engaging end comprises a wider portion that interlocks with the receiving end. When the fastener is locked in the closed loop, the engaging end is confined by the loop. The closed fastener may include: the wider portion of the engaging end trapped by the loop of the receiving end, a first portion of the extended body extending substantially straight from the loop, a bent portion of the extended body at an end of the first portion, and a bowed portion of the extended body defining a curve between the engaging end and the bent portion. In certain embodiments, the closed loop spans a width W from the barbed end confined within the bowl to the bent portion and the bowed portion is spaced apart from the first portion no greater than a depth H. Preferably, 3 cm>W>H, H<6 mm, or both.

In some embodiments, the barbed end comprises one or more barbs and when the fastener is locked in the closed loop, the barbs are retained by the lip that overhangs the opening of the bowl. When the fastener is locked in the closed loop, the barbs are confined within the bowl. The barbed end may include a pushable surface behind the pointed tip.

In some aspects, the invention provides a surgical fastener that includes an extended body, at least a portion of the extended body being flexibly deformable, the extended body terminating at a round end and a receiving end defining a loop. The round end comprises a bulbous shape that requires the loop to elastically deform for the round end to pass through the loop. Bending the deformable portion of the extended body and inserting the round end into the receiving end locks the fastener in a closed loop. In certain embodiments, the closed loop spans a width W from the barbed end confined within the bowl to the bent portion and the bowed portion is spaced apart from the first portion no greater than a depth H. Preferably, 3 cm>W>H, H<6 mm, or both.

In related aspects, the invention provides a surgical fastening device that includes a body with a handle extending therefrom; a trigger on the handle; a shaft extending from the body; a delivery tip at a distal end of the shaft, the delivery tip protruding from the shaft and presenting a tissue-facing surface with an exit port thereon, wherein the delivery tip is biased away from the shaft such that an axis of the shaft and the tissue-facing surface form an acute angle, wherein the delivery tip is bendable towards the axis of the shaft, and wherein the exit port includes a distal end of a delivery slot that carries a non-barbed and non-pointed end of a fastener positioned within the shaft and the exit port is in spatial communication with a distal portion of a guide channel that includes a receiving end of the fastener; a driver member disposed within the shaft, the driver member comprising a shape-memory material that biases the driver member into a curved shape, and wherein when the driver member is disposed within the shaft, the driver member is constrained by the shaft into a straight shape; and at least one fastener having an extended body with a barbed end held by the delivery slot and a receiving end held by the guide slot, wherein the barbed end comprises one or more barbs and a pushable surface engaged with a distal tip of the pushing member, and wherein the receiving end defines a bowl with an opening and a lip that overhangs the opening, wherein operation of the trigger causes the driver member to: push the barbed end of the fastener out of the distal end of the delivery slot, along a curved path to a distal end of the guide slot, and into the receiving end of the fastener such that the one or more barbs are engaged with the lip of the bowl of receiving end, thereby forming the fastener into a closed fastener; release the closed fastener out from a release port; and retract back into the shaft to engage a second fastener.

In some aspects, the invention provides a surgical method of attaching a mesh. The method includes obtaining a surgical fastening device that includes a body with a handle with a trigger extending therefrom; a shaft extending from the body; a delivery tip at a distal end of the shaft; a driver member disposed within the shaft; and a fastener held at the delivery tip. The fastener has an extended body with a barbed end and a receiving end.

The method includes operating the trigger to cause the driver member to: push the barbed end of the fastener out of the delivery tip, along a curved path, and into the receiving end, thereby forming the fastener into a closed fastener; release the closed fastener; and retract back into the shaft and engage a second fastener. Preferably, the delivery tip protrudes from the shaft and presents a tissue-facing surface with an exit port thereon. The fastener is held at the delivery tip at least partially within a delivery slot terminating at the exit port. Preferably, a distal end of the fastener is held within a distal end of a guide slot that extends through the shaft. In preferred embodiments of the method, the delivery tip is biased away from the shaft such that an axis of the shaft and the tissue-facing surface form an acute angle and the driver member comprises a shape-memory material that biases the driver member into a curved shape.

The method includes constraining the driver member in a straight shape by having the driver member disposed within the shaft.

Preferably, the barbed end of the fastener comprises one or more barbs and a pushable surface engaged with a distal tip of the driver member and the receiving end of the fastener defines a bowl with an opening and a lip that overhangs the opening. The barbed end may be held by the delivery slot and the receiving end may be held by the guide slot (e.g., at the distal ends of the delivery and guide slots).

The method may include operating the trigger to cause the driver member to: push the barbed end of the fastener out of the distal end of the delivery slot, along a curved path to the distal end of the guide slot, and into the receiving end of the fastener such that the one or more barbs are engaged with the lip of the bowl of receiving end, thereby forming the fastener into a closed fastener.

Preferably, the method also includes placing the tissue-facing surface against tissue and pulling the trigger, causing the driver member to push the barbed end through a mesh and the tissue and into the receiving end of the fastener outside of the tissue such that the closed fastener spans a width W across a surface of the tissue and penetrates to a depth H within the tissue. The shaft may have a length L of at least 15 cm and has a diameter D of less than 1.55 cm. In preferred embodiments of the method, L≥25 cm and D≤10 mm. Also, H<D<W.

The method may include bending the delivery tip towards the axis of the shaft (e.g., for insertion through a standard trocar or incision during minimally-invasive surgery). Method may include delivering one or more additional fasteners from the shaft, by operating the trigger to deliver a single fastener and advance any remaining fasteners towards the delivery tip.

BRIEF DESCRIPTION OF THE DRAWINGS

FIG. 21A shows the fastener formed into the closed loop.
FIG. 21B shows the open fastener.
FIGS. 21C-21E show the fastener formed into the closed loop.
FIGS. 23A-23E and FIGS. 24A-24E show the fastener deployment (FIGS. 23A-23E provide an isometric view and FIGS. 24A-24E provide a cross sectional view), in which:
FIG. 23A shows positioning the device against a surface of tissue.
FIG. 23B shows the fastener being held within the delivery tip.
FIGS. 23C-23D show the driver member extended from the delivery tip through the tissue.
FIG. 23E shows the closed loop holding a within the tissue.
FIG. 24A shows positioning the device against a surface of tissue (cross sectional view).
FIGS. 24B-24C show the driver member extended from the delivery tip through the tissue (cross sectional view).
FIG. 24D shows the closed loop after the same has been released from the delivery tip (cross sectional view).
FIG. 24E shows the closed loop holding a within the tissue (cross sectional view).

DETAILED DESCRIPTION

Devices and methods for delivering surgical fasteners to a specific depth in tissue and locking the fasteners to secure a mesh to tissue are useful for sacrocolpopexy procedures to treat prolapse conditions such as pelvic organ prolapse. Devices of the invention generally have a body with a handle and an extended shaft dimensioned for minimally invasive surgery. That is, the shaft is preferably smaller in diameter than a standard trocar (e.g., may be <about 15.5 mm in diameter, preferably <10 mm) The shaft is preferably long enough to reach a surgical target, e.g., at least about 15 cm long, preferably at least 25 cm long. The shaft terminates in a delivery tip that presents a tissue-facing surface at an acute angle to an axis of the shaft. Due to this arrangement, when a driver member extends from the shaft while the tissue-facing surface is held against a surface of target tissue, the driver member initially penetrates the tissue at an acute angle (e.g., between about 25° and 65°), which allows the fastener to be wide while limiting penetration depth, minimizing risk of piercing through the tissue (e.g., vagina wall) and providing a reliable attachment. The fastener may be wider than a diameter of a shaft of the device, the fastener is not limited in the width to the diameter of a laparoscopic instrument. Even for fasteners that will penetrate only to a shallow depth, they can be wide (e.g., wider than the penetration depth). The closed loop of the fastener can span a width across the tissue that is wide and therefore strong. In fact, the width can be wider than a diameter of the shaft of the device. The fasteners preferably capture any point or barbs within a smooth bowl once fastened and thus have no sharp edges that would otherwise irritate the nerves and tissue. The driver member is made of a super-elastic material such as Nitinol. Such a material is advantageous because it gives the driver member the strength and shape necessary to allow it to fasten the fastener in the shallow, broad, edge-free configuration useful and beneficial for procedure such as laparoscopic sacrocolpopexy.

Figure 1:
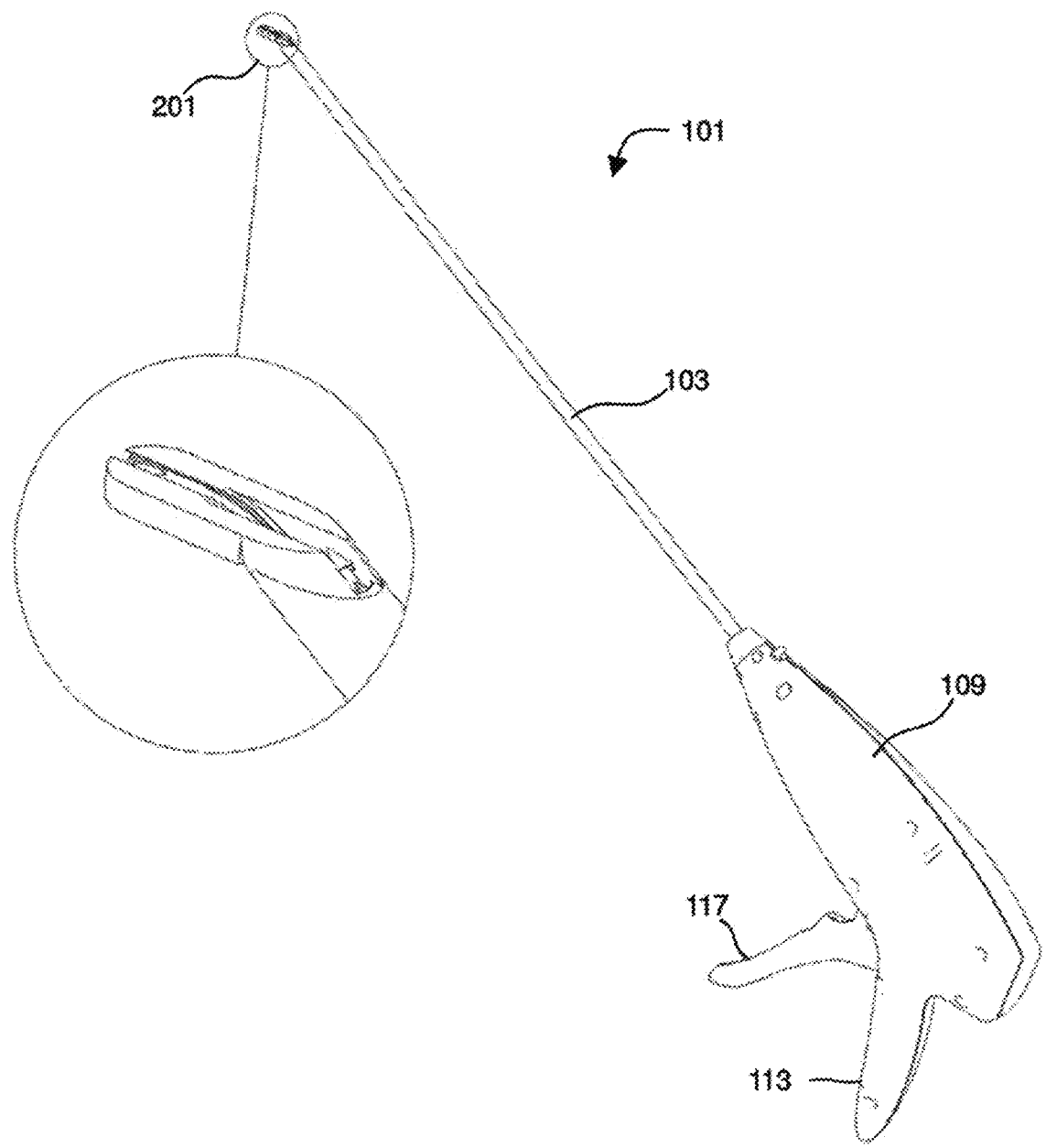
FIG. 1 shows a surgical fastening device.

FIG. 1 shows a surgical fastening device 101. The device 101 includes a body 109 with a handle 113 with a trigger 117 extending therefrom; a shaft 103 extending from the body 109; and a delivery tip 201 at a distal end of the shaft. The trigger 117 is operably engaged with a driver member that extends through shaft 103. Any suitable engagement may be used. For example, the trigger may present a curved, geared surface within the body 109. The curved geared surface may engage a geared slot wheel (through any optional stepper gears that increase or decrease a magnitude of rotation imparted when the trigger 117 is squeezed to rotate about a pivot). The geared slot wheel within handle 109 may include an eccentric slot and a proximal end of the driver member may have a pin engaged into the slot. Squeezing the trigger causes the slot wheel to rotate. The eccentric slot pushes the pin in a direction that includes displacement parallel to an axis of the shaft 103. The displacement of the pin pushes the driver member in a direction distal along shaft 103 and then pull the driver member back in a proximal direction. Thus, squeezing the trigger 117 causes the driver member to translate along the shaft outwards and back to deliver a fastener as described below. A suitable geared trigger with slot wheel and pin that may be modified for use with the invention is shown in U.S. Pat. No. 8,535,339 (e.g., see FIG. 14 and accompanying text), incorporated by reference.

Figure 2:
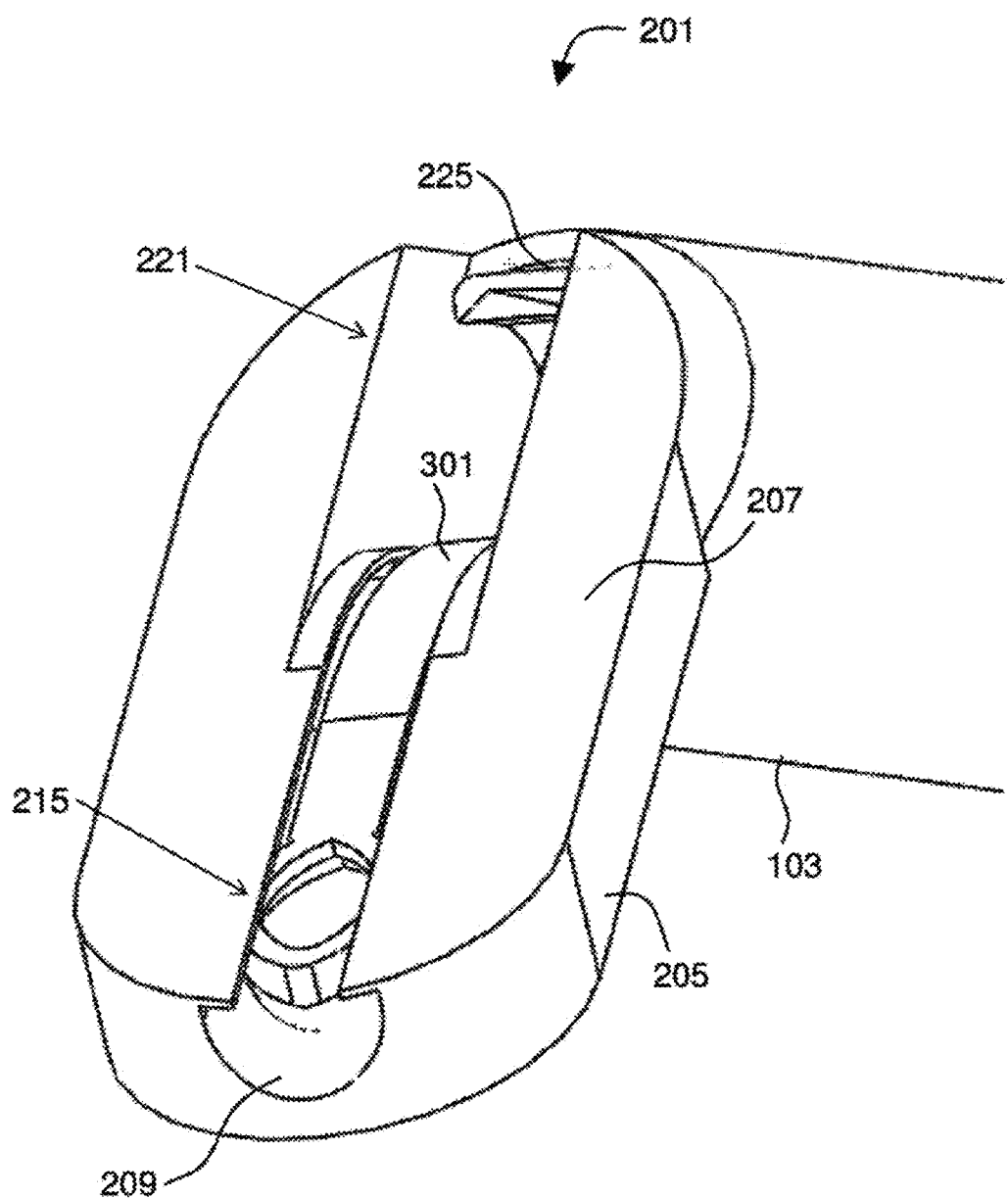
FIG. 2 shows the delivery tip of the device.

FIG. 2 shows the delivery tip 201. The delivery tip 201 includes an extension 205 protruding from the shaft 103 and presenting a tissue-facing surface 207 with an exit port 221 in spatial communication with a guide slot 215. The exit port 221 is proximal to the axis of the shaft and include a distal end of a delivery slot 225. The guide slot 215 extends from within the shaft 103 and curve through the extension 205 and terminates at a release port 209. The delivery slot 225 opens into the exit port 221, which allows a driver member to be pushed outwards from the shaft and through the exit port 221. The delivery tip 201 is biased away from the shaft 103 such that an axis of the shaft and the tissue-facing surface 207 form an acute angle. The guide slot 215 holds an end of a fastener 301 therein.

Figure 3:
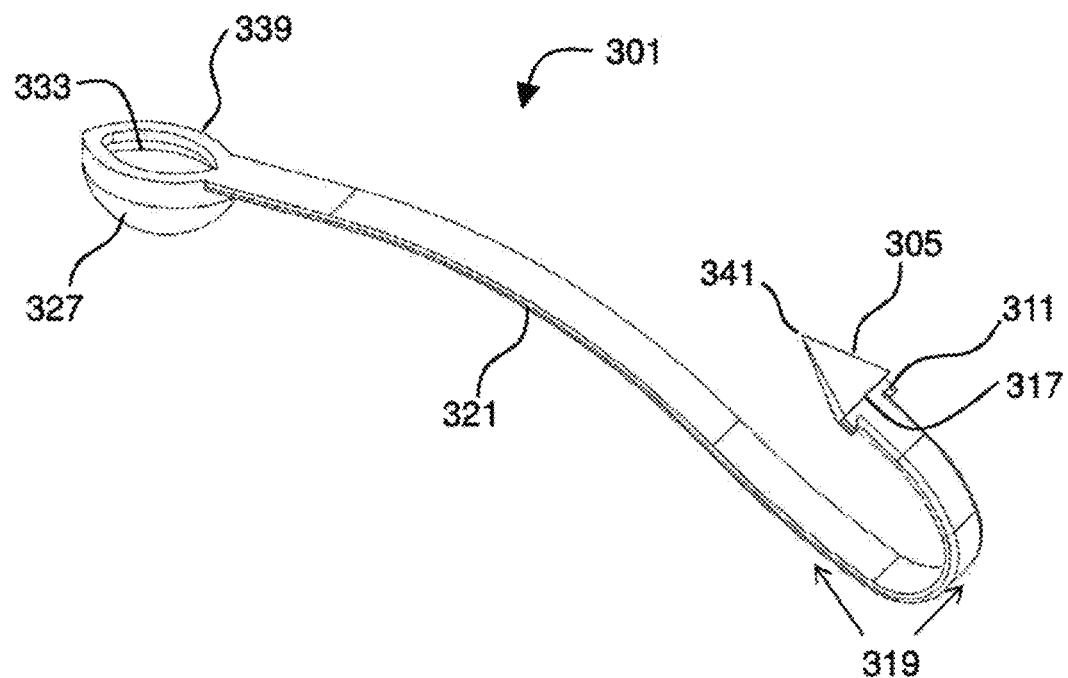
FIG. 3 shows a surgical fastener of the invention.

FIG. 3 shows the surgical fastener 301. The fastener 301 includes an extended body 321, at least a portion 319 of the extended body 321 being flexibly deformable. The extended body 321 terminates at a barbed end 305 and a receiving end 339. Preferably, the receiving end 339 defines a bowl 327 with an opening and a lip 333 that overhangs the opening.

The barbed end 305 may include a pointed tip 341 for piercing through tissue.

Bending the deformable portion 319 of the extended body and inserting the barbed end 305 into the receiving end 339 locks the fastener 301 in a closed loop 401.

The barbed end 305 of the fastener 301 has one or more barbs 311. In preferred embodiments, the barbed end 305 includes one or more pushable surfaces 317 behind the pointed tip 341.

Figure 4:
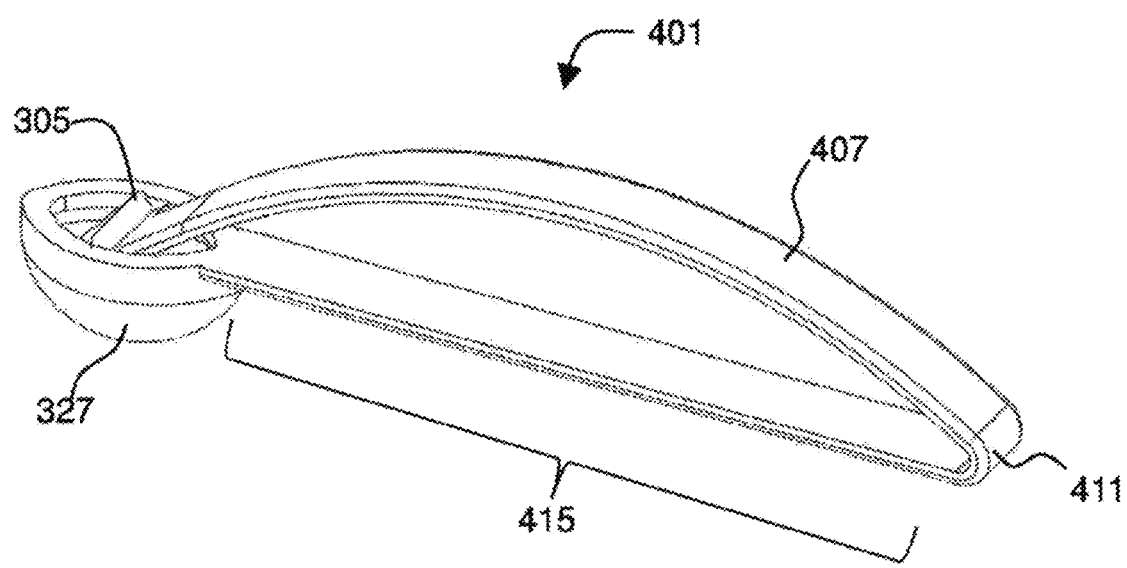
FIG. 4 shows the fastener formed into the closed loop.

FIG. 4 shows the fastener 301 formed into the closed loop 401. When the fastener 301 is locked in the closed loop 401, the pointed tip 341 is confined within the bowl. Preferably, the closed loop 401 includes the barbed end 305 confined within the bowl 327, a first portion 415 of the extended body 321 extending substantially straight from the bowl 327, a bent portion 411 of the extended body 321 at an end of the first portion 415, and a bowed portion 407 of the extended body 321 defining a curve between the barbed end 305 and the bent portion 411. When the fastener 301 is locked in the closed loop 401, the barbs are confined within the bowl 327.

Specifically, when the fastener 301 is locked in the closed loop 401, the barbs 311 are retained by the lip 333 that overhangs the opening of the bowl 327.

Figure 5:
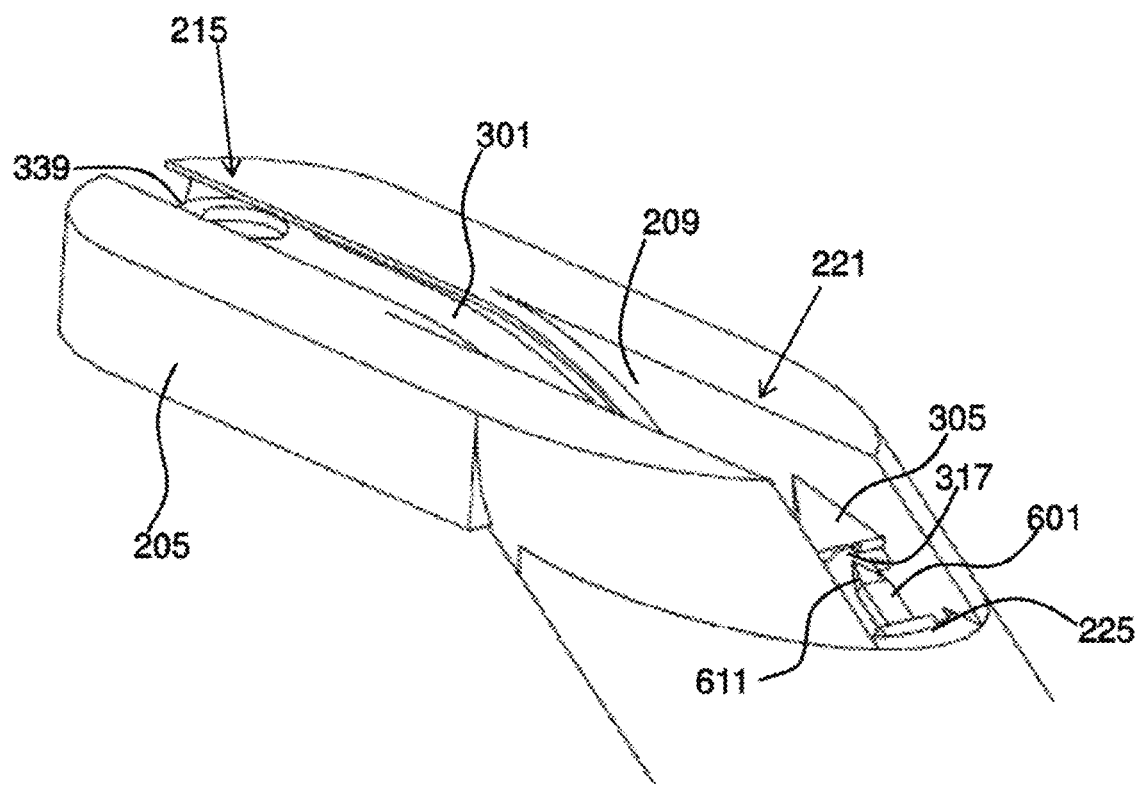
FIG. 5 shows the fastener being held within the delivery tip.

FIG. 5 shows the fastener 301 being held within the delivery tip 201. A driver member 601 is disposed within the shaft 103, in which the driver member 601 is channeled and guided by a delivery slot 225 that extends within the shaft 103. It can be seen that the receiving end 339 of the fastener 301 is held within the guide slot 225. The barbed end 305 of the fastener 301 is held by the delivery slot 225. The pushable surface 317 on the barbed end 305 is oriented to engage with a distal tip 611 of the driver member 601. The exit port 221 defines a space through which the driver member 601 can push the barbed end 305 of the fastener 301 out of the shaft 103.

As shown in FIG. 5, the guide slot 215 holds the receiving end 339 of the fastener 301 and the delivery slot 225 holds the barbed end 305 of the fastener 301. The receiving end 339 is held in place during operation of the device 101 to prevent its retraction back into the shaft 103 due to tension at the fastener. The guide slot 215 is open at a release port 209 on a distal end of the guide slot 215 in order to facilitate release of the closed fastener 401 from the device once the fastener is delivered and locked. Preferably, the guide slot 215 is characterized by having a narrow width along the tissue-facing surface 207 in order to hold the receiving end 339 during its advance along the slot 215. In some embodiments, the device 101 includes a spring-loaded mechanism in the operation handle in order to facilitate faster application which can be necessary for better penetration through tissue.

Figure 6:
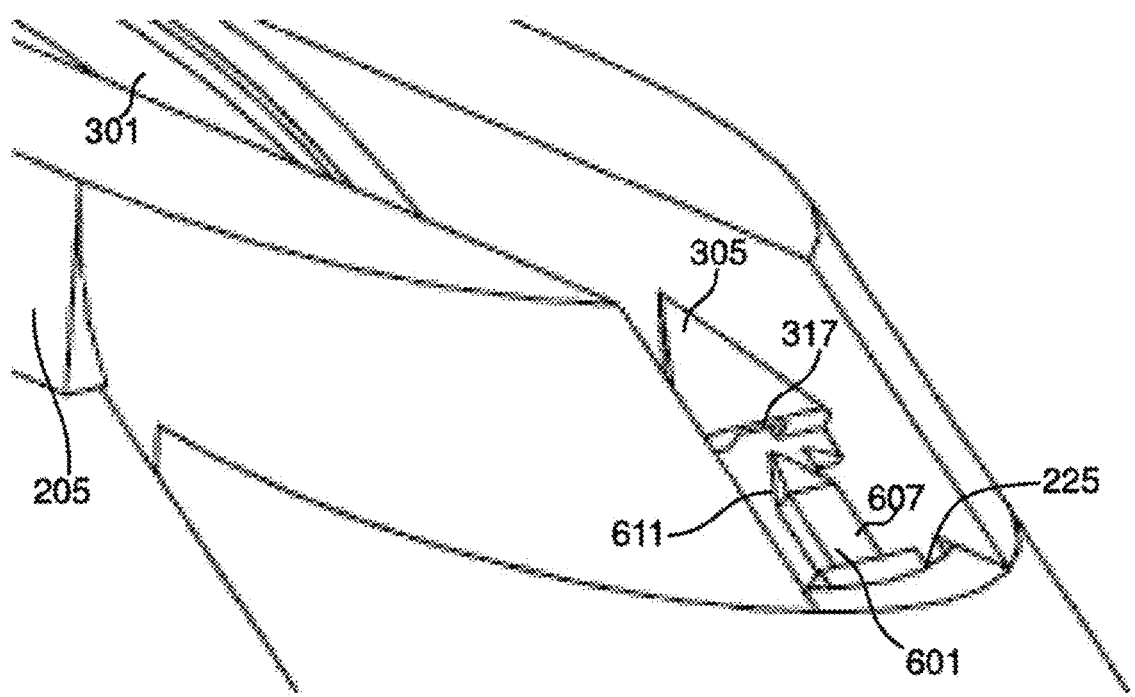
FIG. 6 gives a detailed view of a barbed end of the fastener and a driver member.

FIG. 6 gives a detailed view of the barbed end 305 of the fastener 301 and the distal tip 611 of the driver member 601. The pushable surface 317 includes a recess defined to receive the distal tip 611. The driver member 601 may also include a thinner extension portion 607 to fully engage with the pushable surface 317 on the barbed end 305 of the fastener 301. The barbed end 305 of the fastener 301 has barbs and a pushable surface 317 engaged with a distal tip 611 of the driver member 601 (in FIG. 6, the pushable surface 317 and the distal tip 611 are spaced apart to aid visualization, but one will readily appreciate that the distal tip 611 engages the pushable surface 317). FIGS. 6-10 illustrate operation of the surgical fastening device 101 in response to one operation of the trigger 117.

Pulling the trigger 117 causes the driver member 601 to push the barbed end 305 of the fastener out of the delivery slot 225 on the delivery tip 201, along a curved path, and into the receiving end 339, thereby forming the fastener into a closed fastener 401, release from the closed fastener 401, and retract back into the shaft 103 and engage a second fastener.

Figure 7:
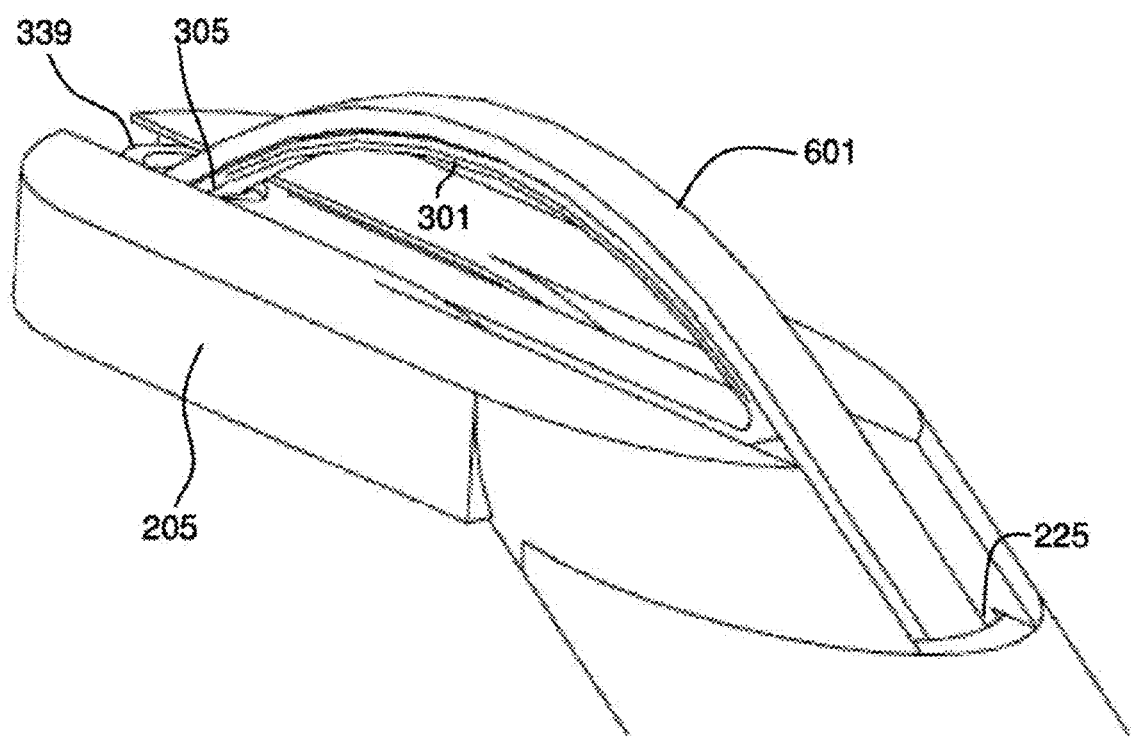
FIG. 7 shows the driver member extended along a curved path.

FIG. 7 shows the driver member 601 extended along a curved path, pushing the barbed end 305 of the fastener 301 into the receiving end 339. It will be appreciated that the driver member 601 includes a shape-memory material that biases the driver member 601 into a curved shape as seen in FIG. 7. When the driver member 601 is disposed within the shaft 103, the driver member 601 is constrained by the delivery slot 225 in the shaft 103 into a straight shape.

Figure 8:
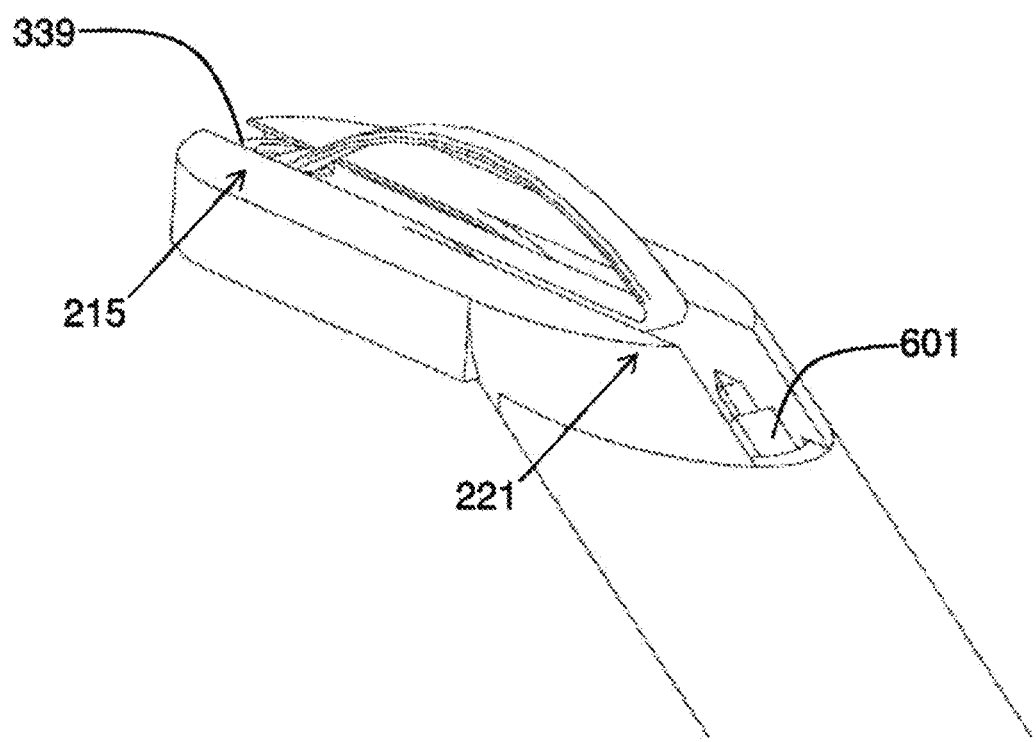
FIG. 8 shows the driver member released from the closed fastener.

FIG. 8 shows the driver member 601 released from the closed fastener 401. Specifically, operation of the trigger 117 has caused the driver member 601 to push the barbed end 305 of the fastener 301 out of the exit port 221 on the delivery tip 201, along a curved path and into the receiving end 339 held within the guide slot 215, such that the one or more barbs 311 are engaged with the lip 333 of the bowl 327 of receiving end 339, thereby forming the fastener 301 into a closed fastener 401.

Figure 9:
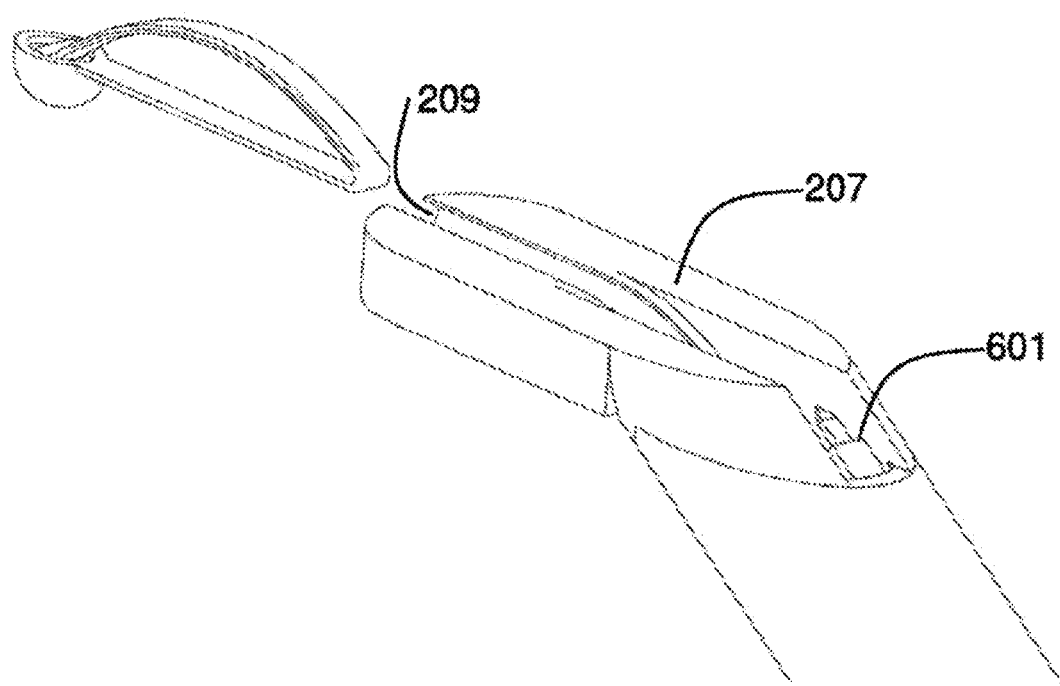
FIG. 9 shows the closed fastener released from the delivery slot.

FIG. 9 shows the closed fastener 401 released through the release port 209 as the driver member 601 retracts back into the shaft 103 and engage a second fastener.

An important feature of the surgical fastening device 101 is the control over delivery depth and the fastening strength that are afforded by the particular dimensional relationships of the fastener 301 and the device 101. Placing the tissue-facing surface 207 against tissue and pulling the trigger 117 causes the driver member 601 to push the barbed end through the tissue and into the receiving end 339 of the fastener back on the outside of the tissue, forming the fastener 301 into the closed loop 401.

Figure 10:
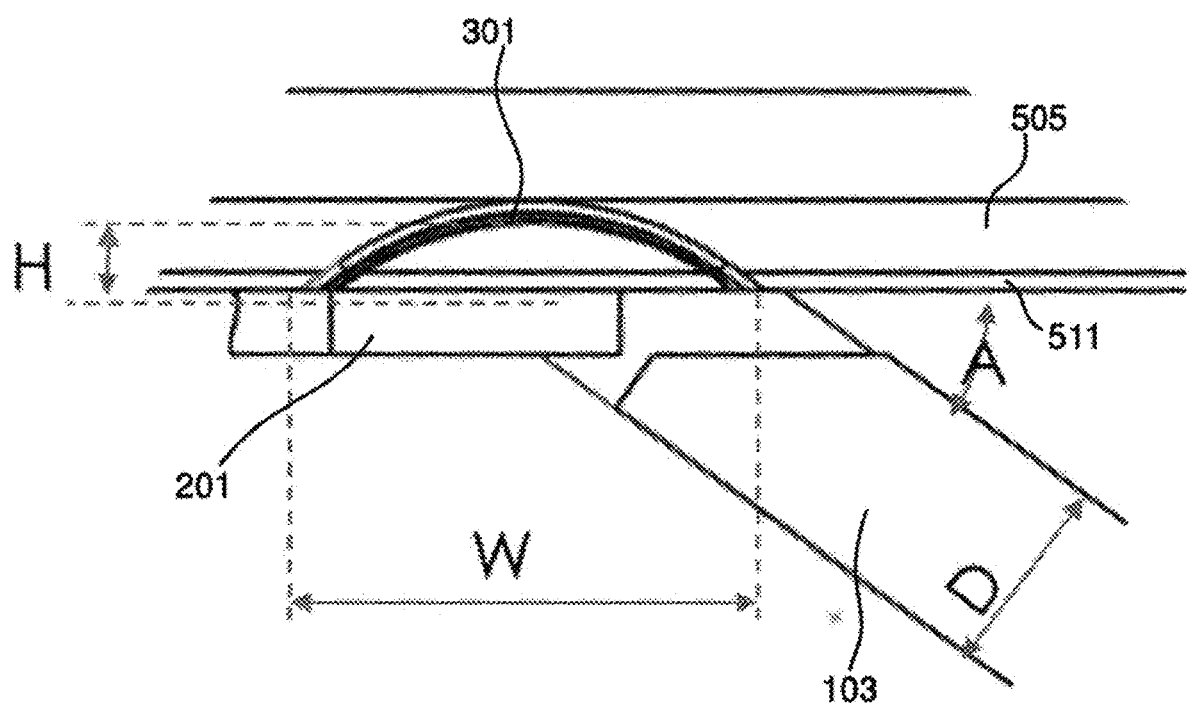
FIG. 10 shows a fastener formed into the closed loop.

FIG. 10 shows a fastener 301 formed into the closed loop 401 with the delivery tip 201 still in place against tissue 505. Here, the device 101 has been used to fasten a mesh 511 to the tissue 505. The shaft 103 is positioned such that the tissue-facing surface 207 of the delivery tip 201 faces the mesh 511 and a surface of the tissue 505. The closed fastener 401 spans a width W across a surface of the tissue and penetrates to a depth H within the tissue. Because the delivery tip 201 is biased away from the shaft 103 such that an axis of the shaft 103 and the tissue facing surface 207 form an acute angle, A, the shaft 103 forms the angle A with the surface of the tissue 505. In preferred embodiments, the shaft is dimensioned for minimally-invasive surgery and has a length L of at least 15 cm and has a diameter D of less than 1 cm. More preferably, L≥25 cm and D≤7 mm Most preferably, H<D<W.

Figure 11:
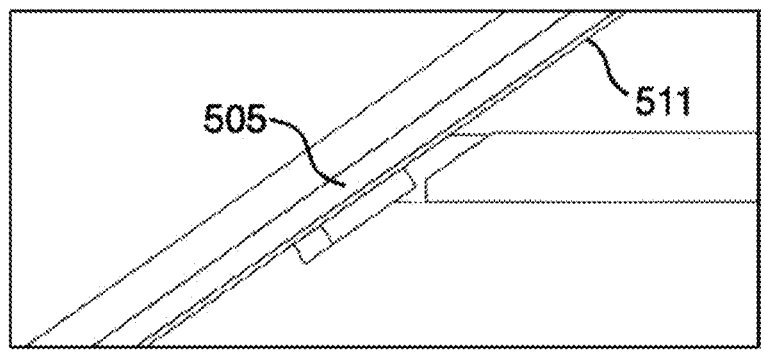
FIG. 11 shows positioning the device against a surface of tissue.
Figure 12:
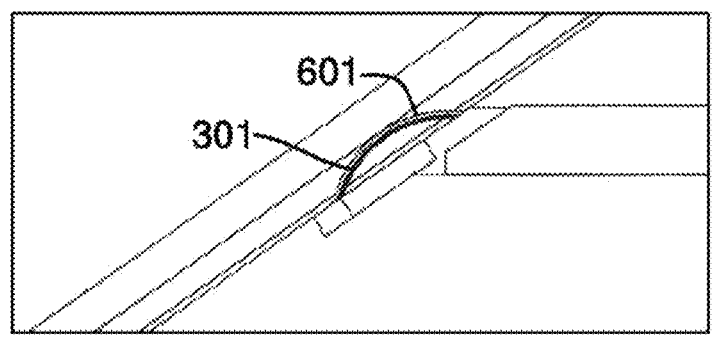
FIG. 12 shows the driver member extended through the tissue.
Figure 13:
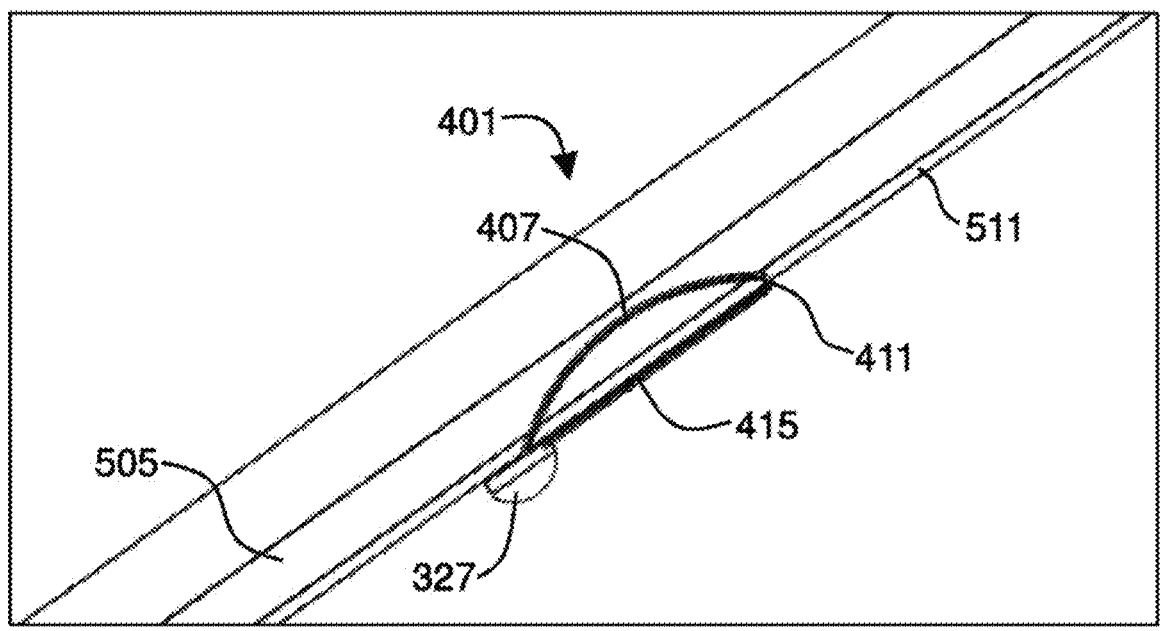
FIG. 13 shows the closed loop holding a mesh to the tissue.

FIGS. 11-13 show operation of the device 101.

FIG. 11 shows positioning the tissue-facing surface 207 against a surface of tissue 505, and specifically against a mesh 511 to be fastened to the tissue.

FIG. 12 shows the driver member 601 extended through the tissue 505 to form the fastener 301 into the closed loop 401.

FIG. 13 shows the closed loop 401 holding the tissue 511 to the tissue 505. The closed loop 401 includes the barbed end 305 confined within the bowl 327, a first portion 415 of the extended body 321 extending substantially straight from the bowl 327, a bent portion 411 of the extended body 321 at an end of the first portion 415, and a bowed portion 407 of the extended body 321 defining a curve extending through the tissue 505 between the barbed end 305 and the bent portion 411. For successfully surgical procedures, the closed fastener 401 preferably spans a width W from the barbed end 305 confined within the bowl 327 to the bent portion 411 and the bowed portion 407 is preferably spaced apart from the first portion 415 no greater than a depth H. In preferred embodiments, 3 cm>W>H. Additionally or alternatively, it may be preferable that H<6 mm.

As discussed above, pulling the trigger 117 causes the device 101 to form the fastener into a closed fastener 401, release from the closed fastener 401, and retract back into the shaft 103 and engage a second fastener.

Figure 14:
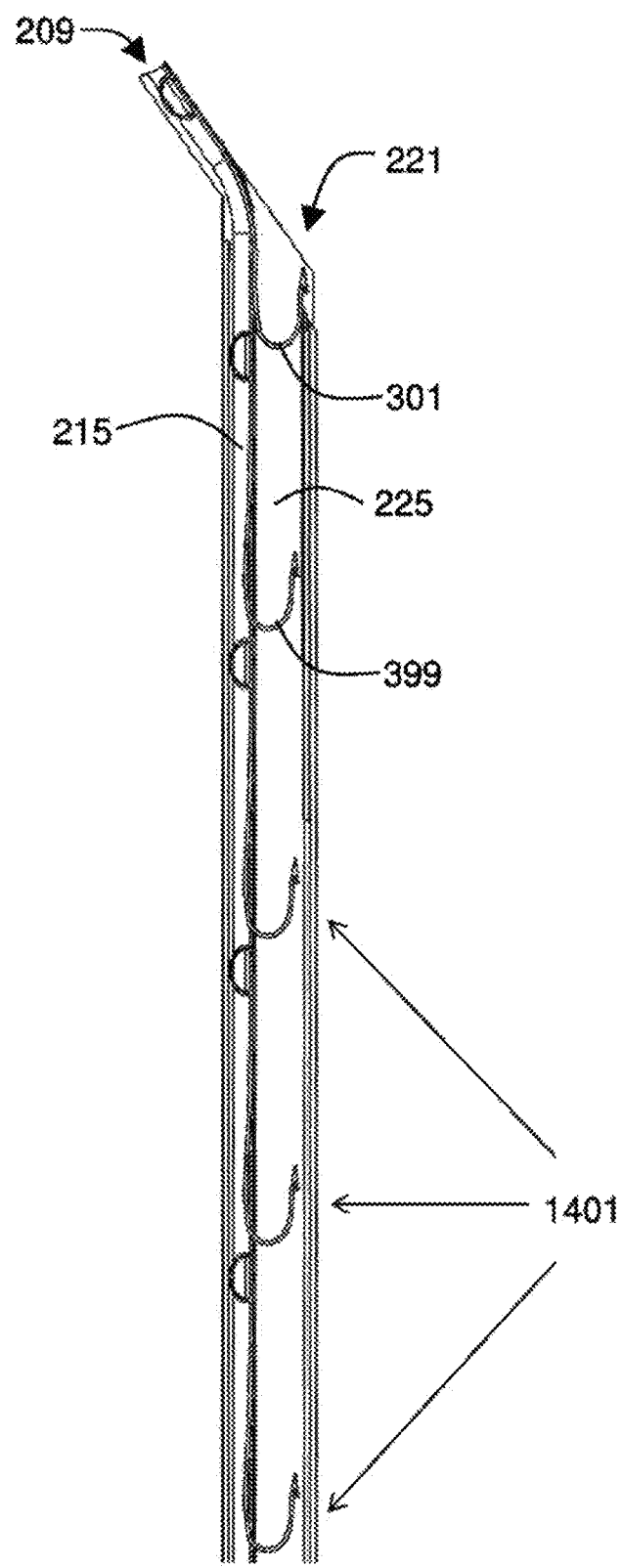
FIG. 14 shows a device loaded with multiple fasteners.

FIG. 14 shows a device 101 loaded with the fastener 301, a second fastener 399, and three additional fasteners 1401 disposed with the shaft. Visible within shaft 103 are the delivery slot 225 extending to the exit port 221 and also the guide slot 215 extending to the release port 209. Each fastener 301 is held within the shaft 103 in an open configuration, with the receiving end held in the guide slot 215 and the barbed end 205 held in the delivery slot 225. The device 101 may be loaded with any suitable number of the fasteners 301. Each operation of the trigger delivers a single fastener and advances the additional fasteners towards the delivery tip.

For minimally-invasive surgery, it may be preferable for the delivery tip 201 to be bendable towards the axis of the shaft 103, i.e., so that the extended shaft may most easily pass through a standard surgical trocar.

Figure 15:
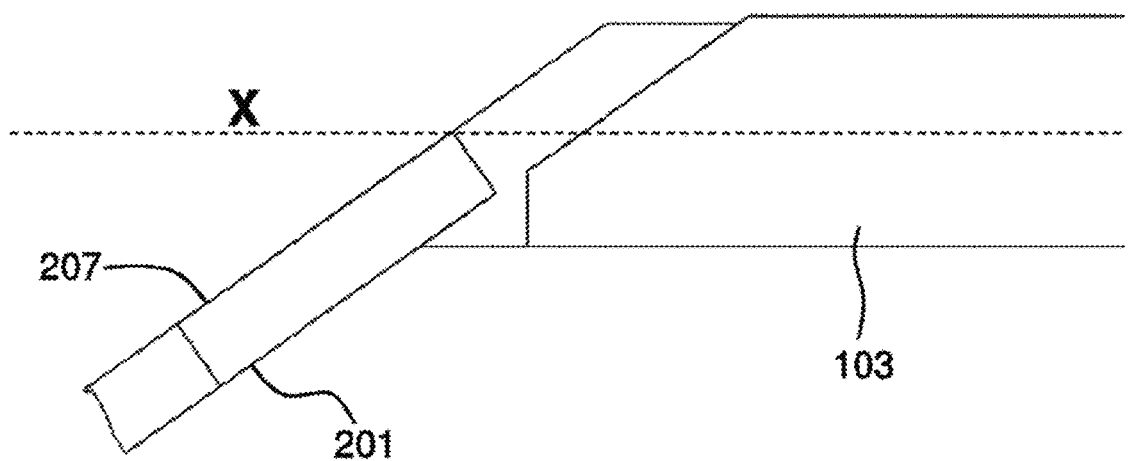
FIG. 15 is a profile of the delivery tip.

FIG. 15 is a profile of the delivery tip 201. It can be seen that the delivery tip 201 is biased away from the shaft 103 such that an axis X of the shaft 103 and the tissue-facing surface 207 form an acute angle. It may be preferable to be able to deform the delivery tip 201, e.g., for ease of insertion of the shaft 103 through a standard surgical trocar.

Figure 16:
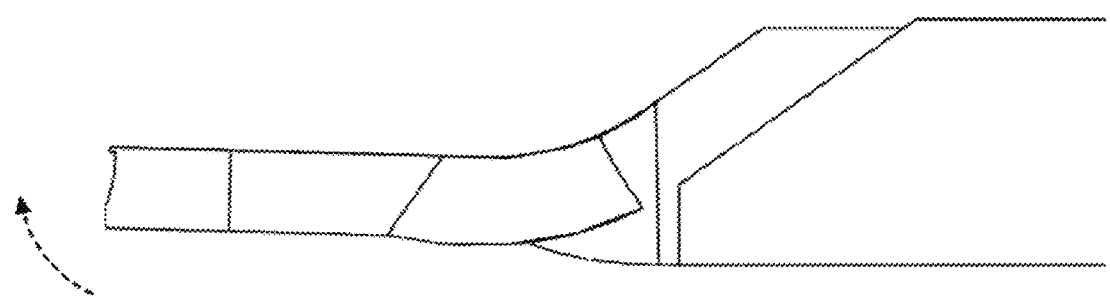
FIG. 16 shows the delivery tip bent.

FIG. 16 shows the delivery tip 201 bent towards the axis X.

Figure 17:
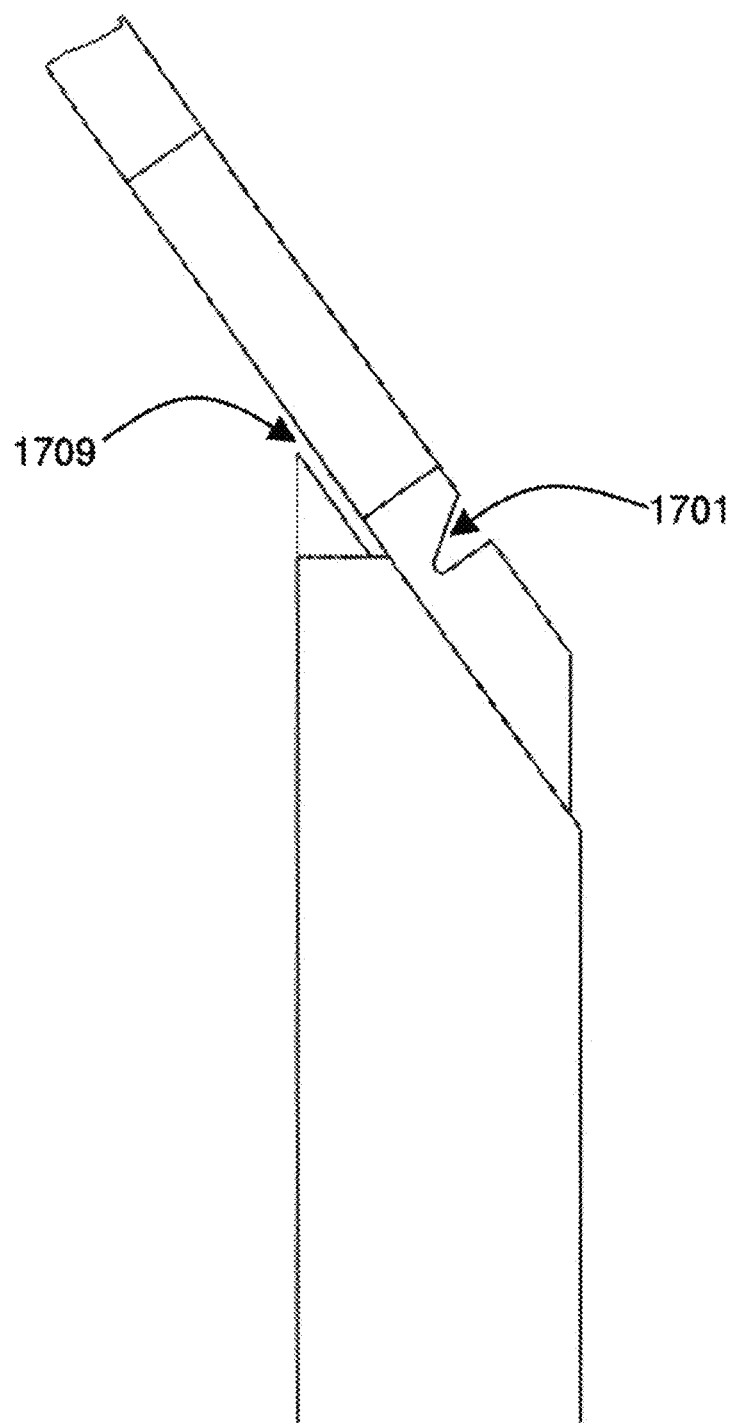
FIG. 17 shows slits that may be included so that the delivery tip.

FIG. 17 shows a compression slit 1701 and an expansion slit 1709 that may be included so that the delivery tip 201 may be more readily bent towards the axis X of the shaft 103. It will be appreciated that the axis X is an idealized geometrical concept defined by the generally cylindrical nature of the shaft 103 and that there need not be any tangible shaft axis. The axis X is referred to so that one may comprehend the configuration of the delivery tip 201.

Thus it can be seen that the disclosure includes a surgical fastening device 101 that includes a body 109 with a handle 113 extending therefrom; a trigger 117 on the handle; a shaft 103 extending from the body; a delivery tip 201 at a distal end of the shaft 103, the delivery tip 201 protruding from the shaft 103 and presenting a tissue-facing surface 207 with an exit port 221 and a guide slot 215, wherein the delivery tip 201 is biased away from the shaft 103 such that an axis of the shaft 103 and the tissue-facing surface 207 form an acute angle, wherein the delivery tip 201 is bendable towards the axis of the shaft 103, and wherein the exit port 221 includes an end of a delivery slot 225; a driver member 601 disposed within the shaft 103, the driver member 601 comprising a shape-memory material that biases the driver member 601 into a curved shape, wherein when the driver member 601 is disposed within the shaft 103, the driver pushing member 601 is constrained by the shaft 103 into a straight shape; and at least one fastener 301 held at the delivery tip 201 at least partially within a guide slot 215, the fastener having an extended body 321 with a barbed end 305 and a receiving end 339, wherein the barbed end 305 comprises one or more barbs 311 and a pushable surface 317 engaged with a distal tip 611 of the driver member 601, and wherein the receiving end 339 defines a bowl 327 with an opening and a lip 333 that overhangs the opening, wherein operation of the trigger 117 causes the driver member 601 to: push the barbed end 305 of the fastener 301 out of the exit port 221, along a curved path to the receiving end 339 being held by the guide slot 215, and into the receiving end 339 of the fastener 301 such that the one or more barbs 311 are engaged with the lip 333 of the bowl 327 of the receiving end 339, thereby forming the fastener 301 into a closed fastener 401, release the closed fastener from a release port 209, and, retract back into the shaft 103 to engage a second fastener 399.

Figure 20:
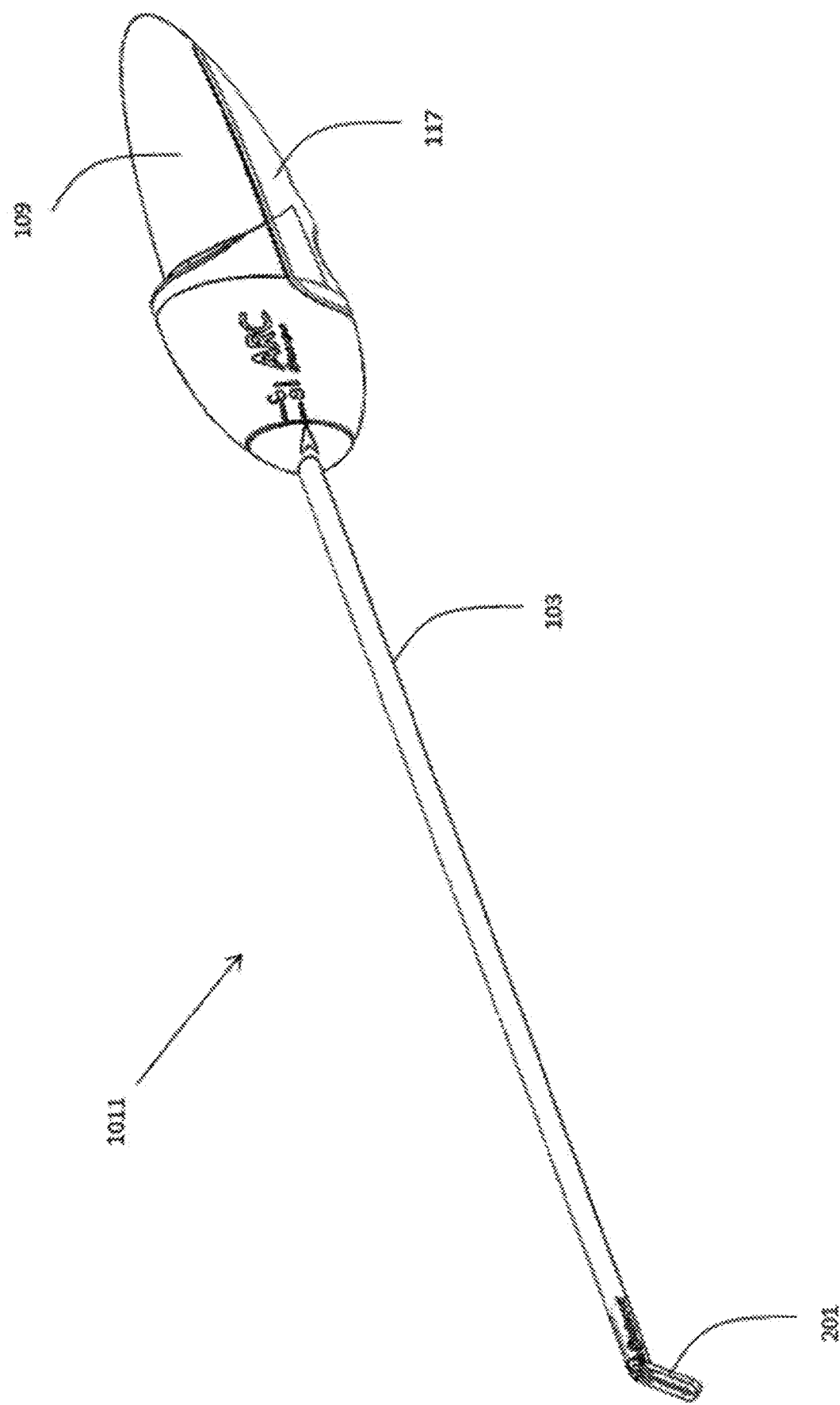
FIG. 20 shows a surgical fastening device according to a second embodiment of the present invention.

Reference is now made to FIG. 20 which illustrates another embodiment of the present invention.

FIG. 20 shows a surgical fastening device 1011. The device 1011 includes a body 109 with a trigger 117 extending therefrom; a shaft 103 extending from the body 109; and a delivery tip 201 at a distal end of the shaft. The trigger 117 is operably engaged with a driver member that extends through shaft 103. Any suitable engagement may be used. For example, the trigger may present a curved, geared surface within the body 109. The curved geared surface may engage a geared slot wheel (through any optional stepper gears that increase or decrease a magnitude of rotation imparted when the trigger 117 is squeezed to rotate about a pivot). The geared slot wheel within body 109 may include an eccentric slot and a proximal end of the driver member may have a pin engaged into the slot. Squeezing the trigger causes the slot wheel to rotate. The eccentric slot pushes the pin in a direction that includes displacement parallel to an axis of the shaft 103. The displacement of the pin pushes the driver member in a direction distal along shaft 103 and then pull the driver member back in a proximal direction. Thus, squeezing the trigger 117 causes the driver member to translate along the shaft outwards and back to deliver a fastener as described below.

A suitable geared trigger with slot wheel and pin that may be modified for use with the invention is shown in U.S. Pat. No. 8,535,339 (e.g., see FIG. 14 and accompanying text), incorporated by reference.

FIGS. 21A-21E show the surgical fastener 301, according to the second embodiment. The fastener 301 includes an extended body 321, at least a portion 319 of the extended body 321 being flexibly deformable. The extended body 321 terminates at a loop-like receiving end 339 and an opposite end 3055 (e.g., with an engagement feature). The depicted engagement feature at opposite end according to this embodiment is not barbed and does not include any sharp ends.

According to this embodiment the surgical fastener 301 is made of at least one piece of a monofilament suture or a multifilament (braided) suture.

The shape of said surgical fastener 301 can be achieved by ultrasonic welding or glued or any other welding methods known (e.g., laser welding, RF welding, friction welding).

Figure 21A:
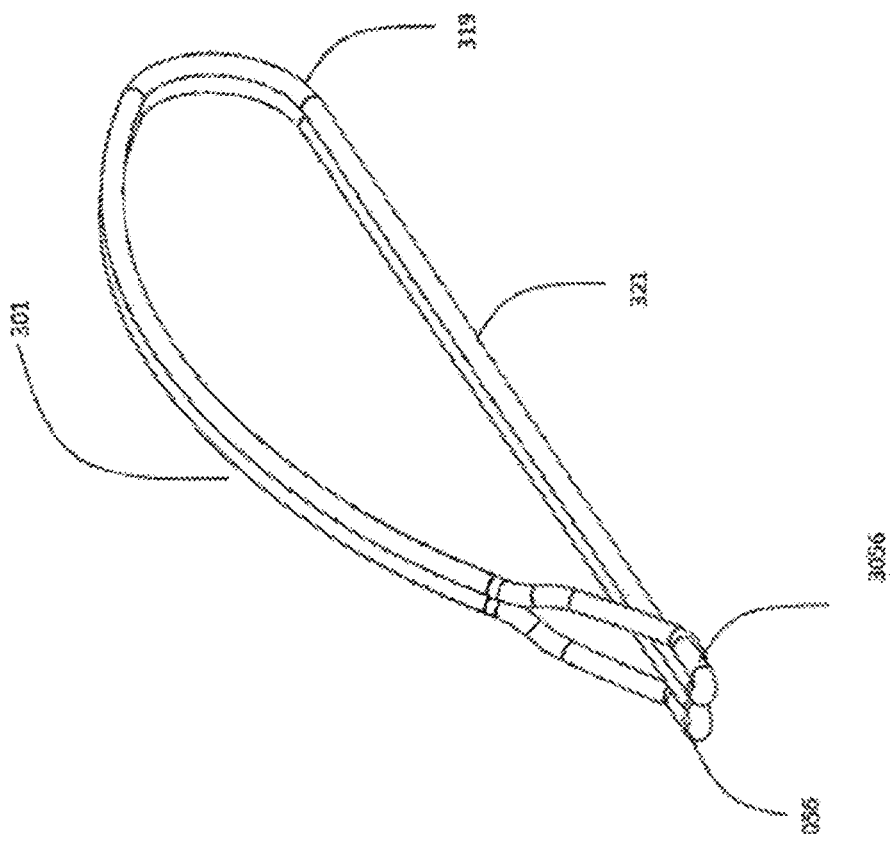
FIGS. 21A-21E show the surgical fastener according to a second embodiment of the present invention.

It is noted that bending the deformable portion 319 of the extended body and inserting the receiving end 339 into the opposite end 3055 locks the fastener 301 in a closed loop (see FIG. 21A).

Figure 21B:
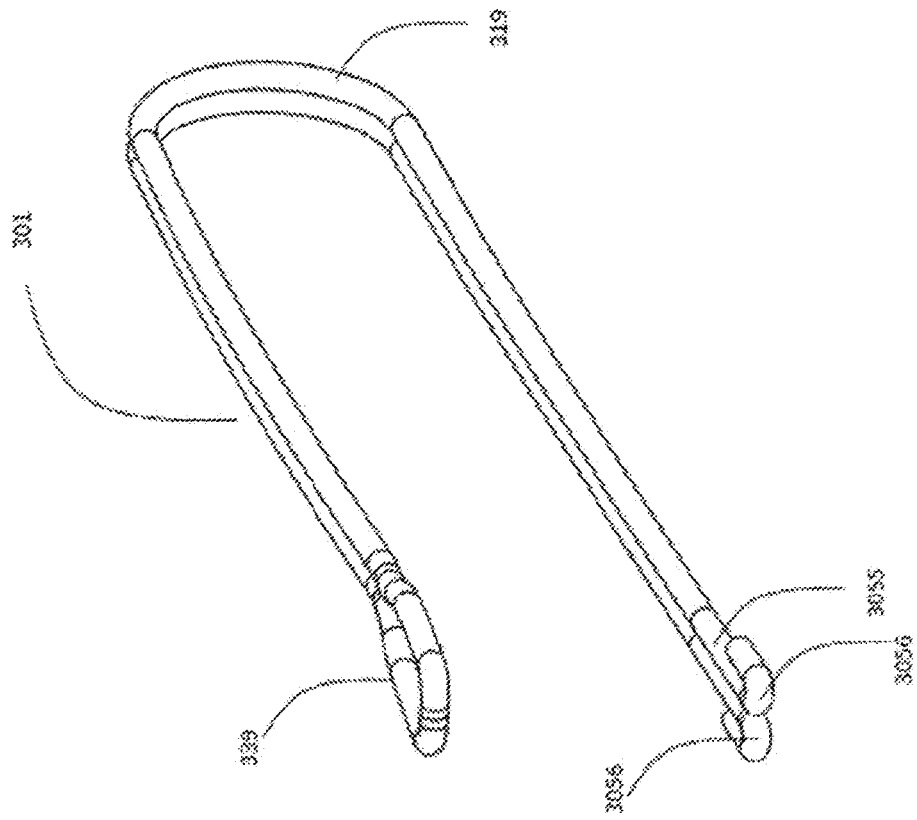

FIG. 21A shows the surgical fastener 301 in the closed loop while FIG. 21B shows the surgical fastener 301 in the open position. Is should be noted that in those embodiments the ends 3056 of the opposite end of the fastener are bended thereon.

Figure 21C:
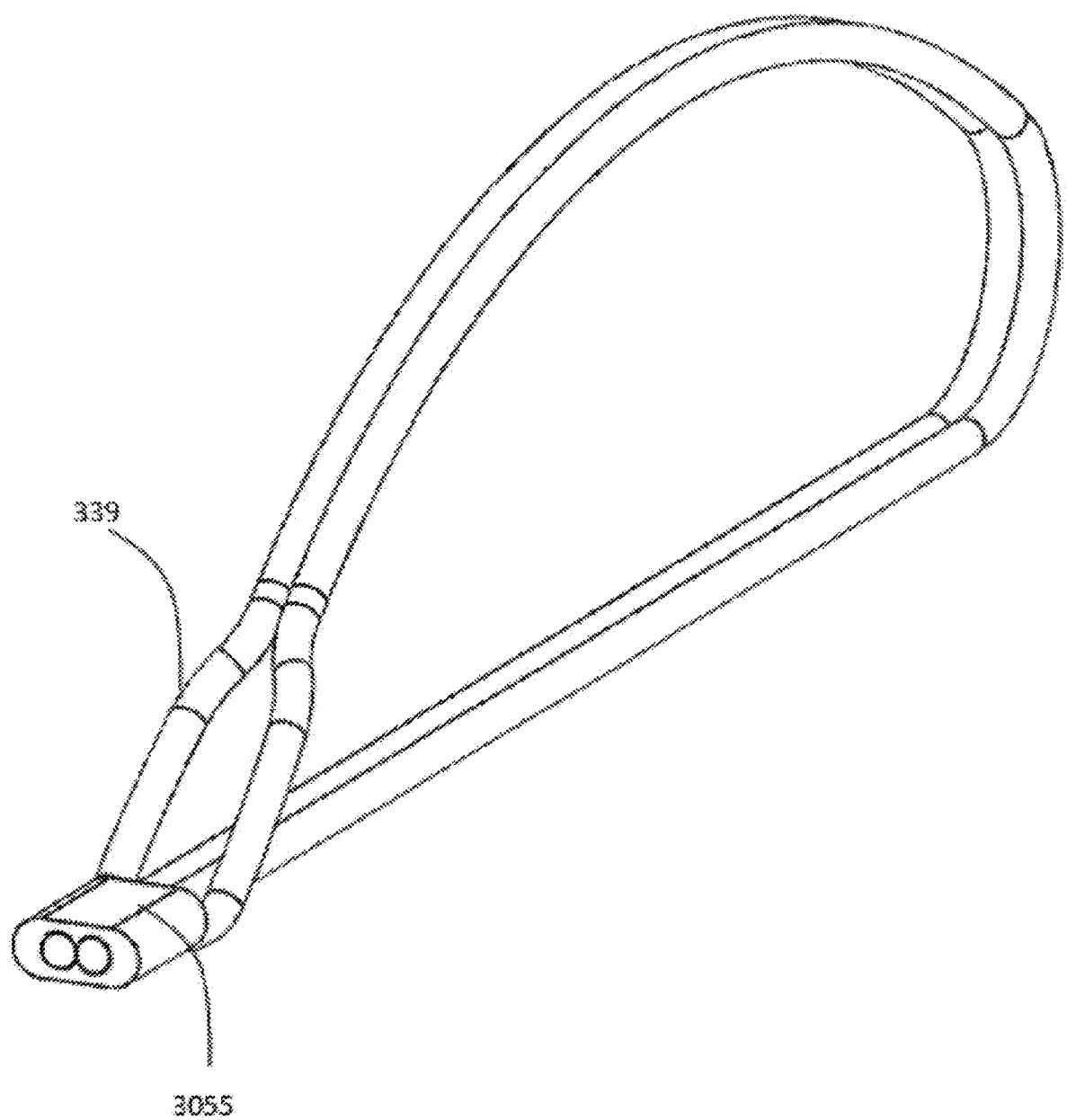
Figure 21D:
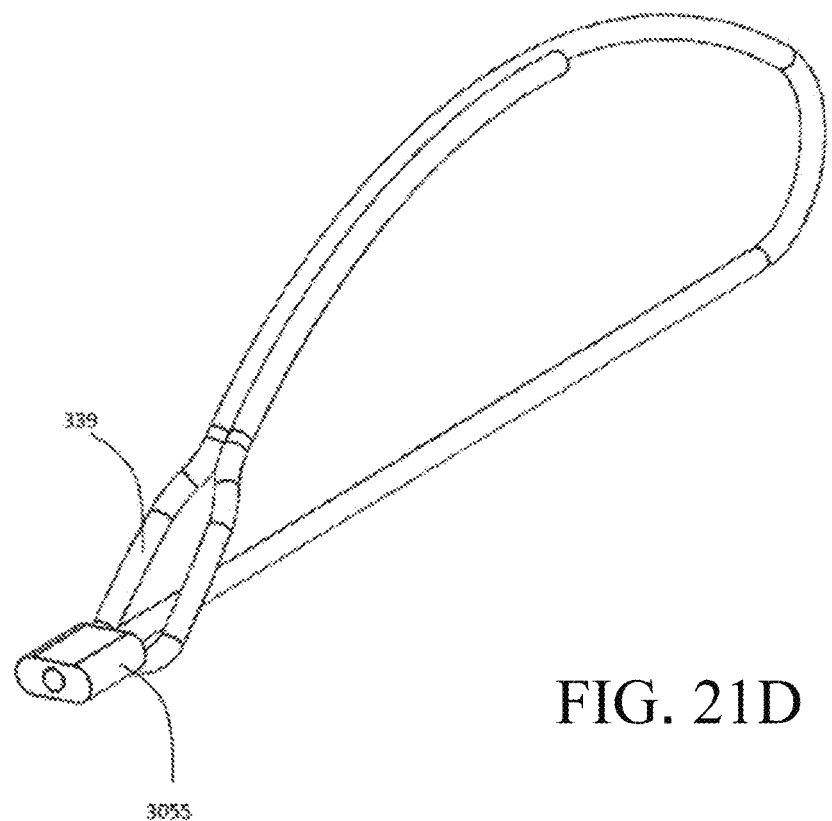

FIGS. 21C-21D show another embodiment of the opposite end 3055 of the surgical fastener 301. In this embodiment, the opposite end 3055 is shaped as a locker similar to a cable end.

Figure 21E:
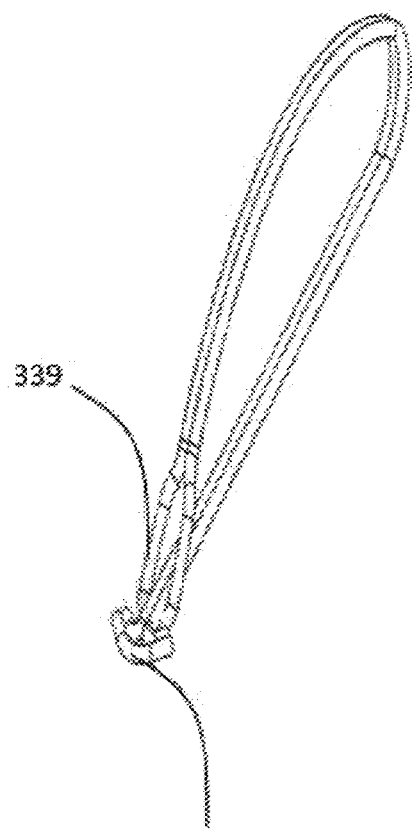

FIG. 21E show another embodiment of the opposite end 3055 of the surgical fastener 301. In this embodiment, the opposite end 3055 is shaped as curved arrow.

Figure 22:
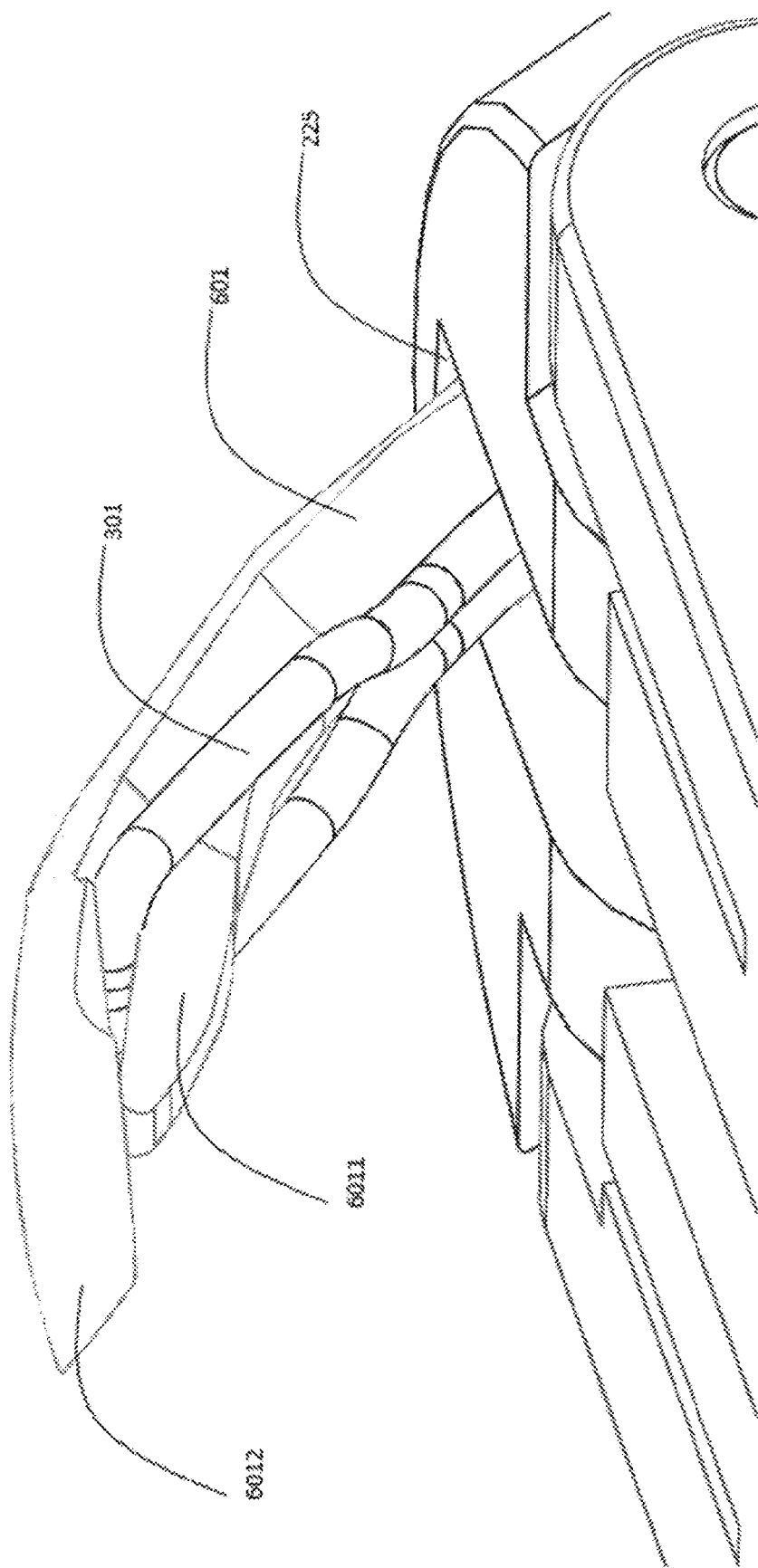
FIG. 22 shows the driver member according to a second embodiment of the present invention.

FIG. 22 shows the driver member 601 according to the second embodiment of the present invention. According to this embodiment, the driver member 601 is characterized by a sharp tip 6012 adapted to penetrate a tissue.

According to this embodiment, the driver member 601 comprises at least one hook 6011 which is adapted to engage with the loop-like receiving end 339 of the fastener 301. The hook 'swipes' receiving end 339 when the same extends out of the delivery tip 201, such that the receiving end 339 of said fastener 301 is enclosed by said hook 6011 and the sharp tip 6012 of the driver member 601.

It should be noted that the driver member 601, before extending from the delivery end 201, is disposed within the shaft 103, in which the driver member 601 is channeled. The shaft 103 ends in delivery slot 225 throughout which the driver member 601 exits the shaft. It should also be noted that at least one fastener 301 is held is disposed within the shaft 103, such that hook 6011 of driver member 601 "grabs" the receiving end 339 and expends out of the delivery end 201. The opposite end 3055 of the fastener 301 is oriented to engage with a receiving end 339.

Reference is now made to FIGS. 23A-23E and 24A-24E which show operation of the device 1010; namely the fastener 301 deployment, in response to one operation of the trigger 117.

Pulling the trigger 117 causes the driver member 601 to grasp the receiving end 339 of the fastener out of the delivery slot 225 on the delivery tip 201, along a curved path, and into the opposite end 3055, thereby forming the fastener into a closed fastener, released from the closed fastener, and retract back into the shaft 103 and engage a second fastener.

Figure 23A:
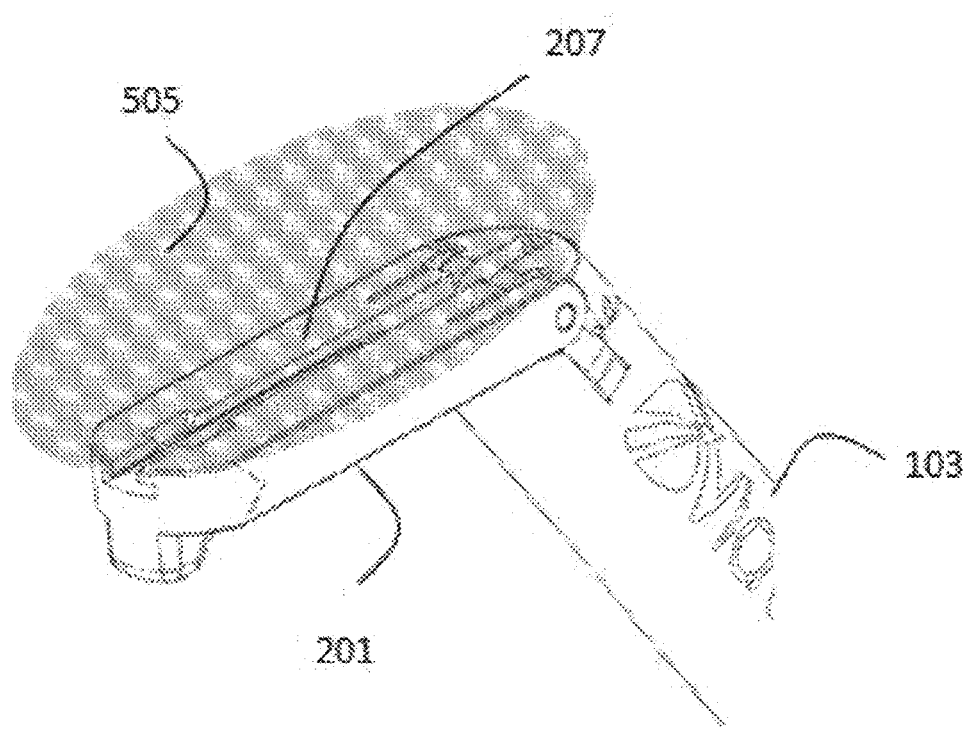

FIG. 23A illustrates the tissue facing surface 207 of the delivery tip 201 held against the tissue 505 (not shown in the rest of the figures, for clarity purposes).

Figure 23B:
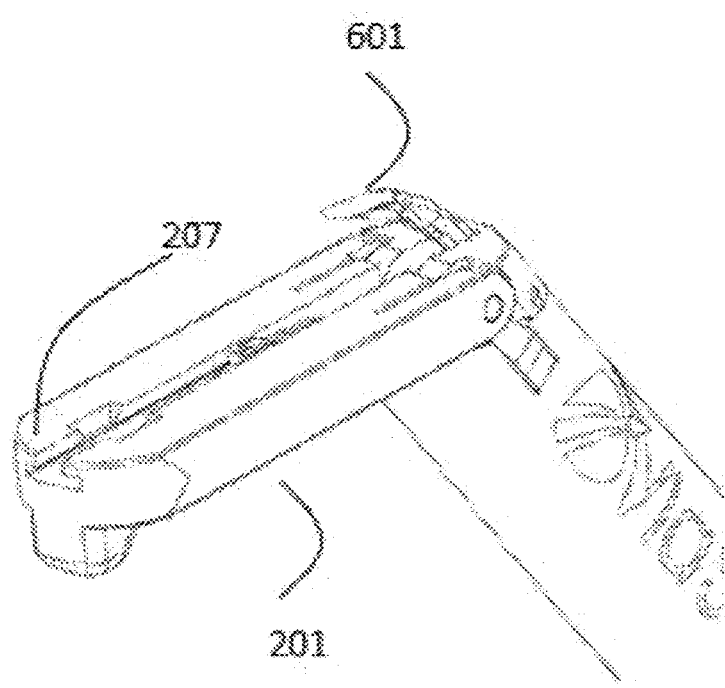

FIG. 23B illustrates the driver member 601 "grabs" the receiving end 339 and expends out of the shaft 103 in delivery end 201 throughout delivery slot 225.

Figures 23C, 23D:
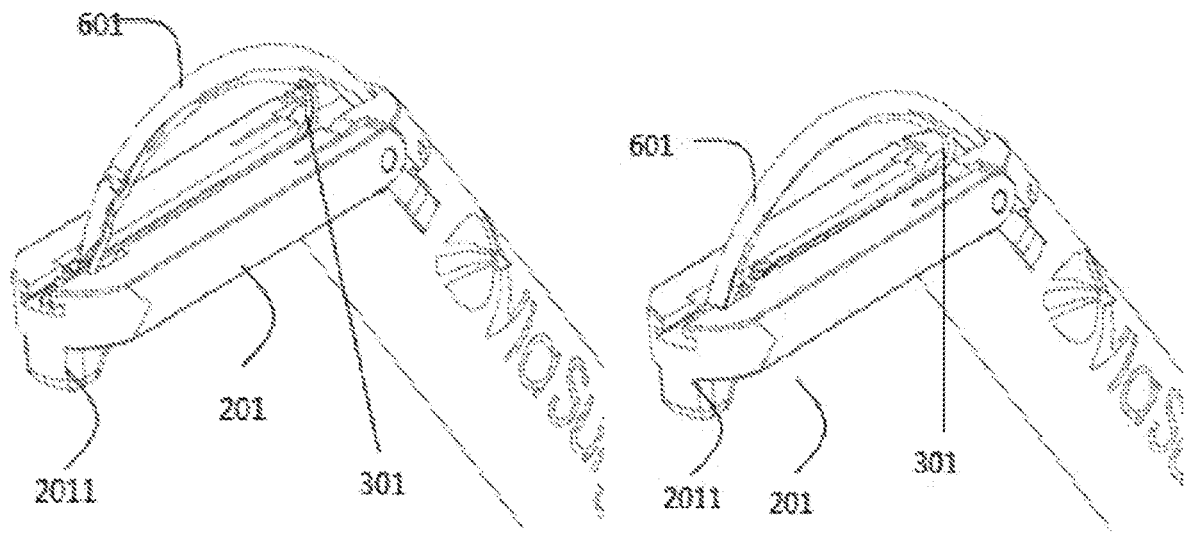

FIGS. 23C-23D illustrate the driver member 601 and the receiving end 339 approaching the delivery tip's distal end 2011. The distal end 2011 is shaped as a bowl so that both the driver member 601 (with receiving end 339 engaged therewith) and the opposite end 3055 of the fastener 301 can engage together to form the closed loop.

Figure 23E:
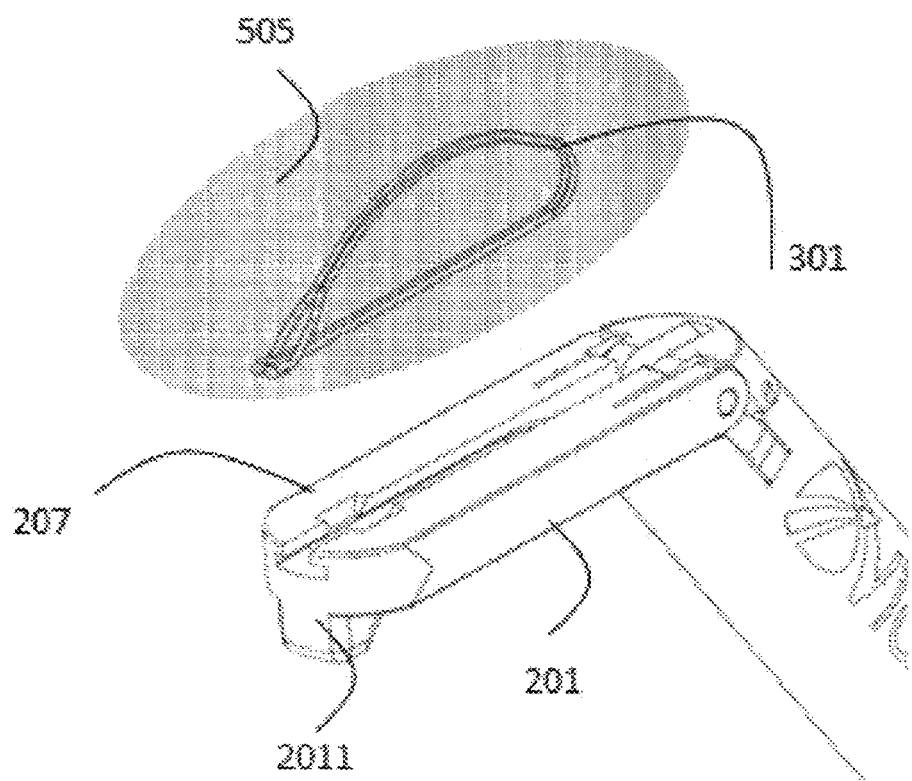

FIG. 23E shows the closed fastener released in tissue 505 and the driver member 601 retracts back into the shaft 103 to engage with a second fastener.

Reference is now made to FIGS. 24A-24E which show operation of the device 1010; namely the fastener 301 deployment, in response to one operation of the trigger 117, in a cross sectional view.

As mentioned above, activating trigger 117 causes the driver member 601 to grasp the receiving end 339 of the fastener out of the delivery slot 225 on the delivery tip 201, along a curved path, and into the opposite end 3055, thereby forming the fastener into a closed fastener, released from the closed fastener, and retract back into the shaft 103 and engage a second fastener.

Figure 24A:
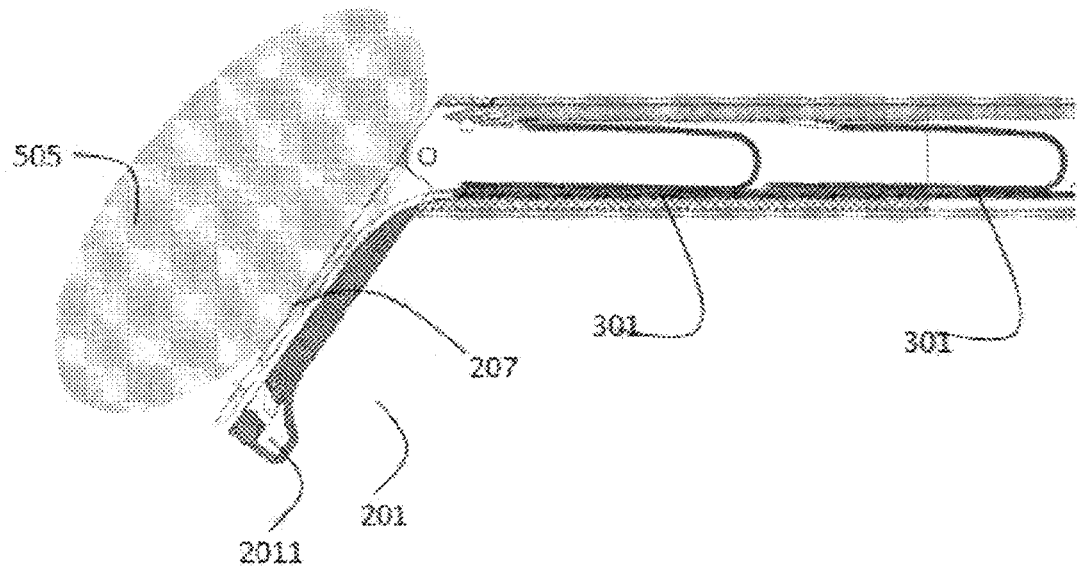

FIG. 24A illustrates the tissue facing surface 207 of the delivery tip 201 held against the tissue 505 (not shown in the rest of the figures, for clarity purposes).

Figure 24B:
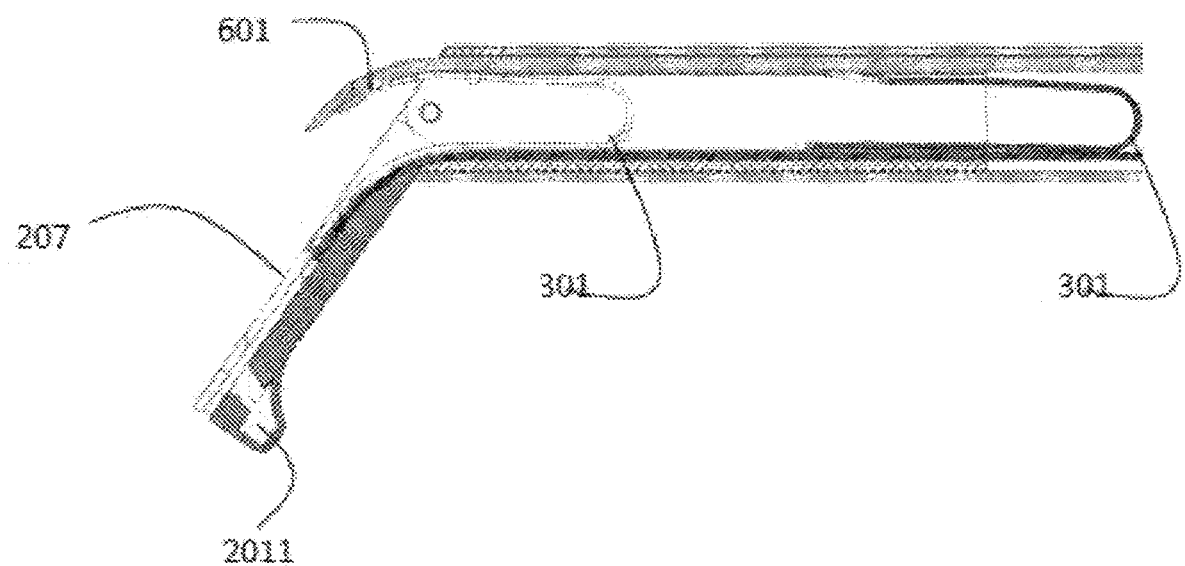

FIG. 24B illustrates the driver member 601 "grabs" the receiving end 339 and expends out of the shaft 103 in delivery end 201 throughout delivery slot 225.

Figure 24C:
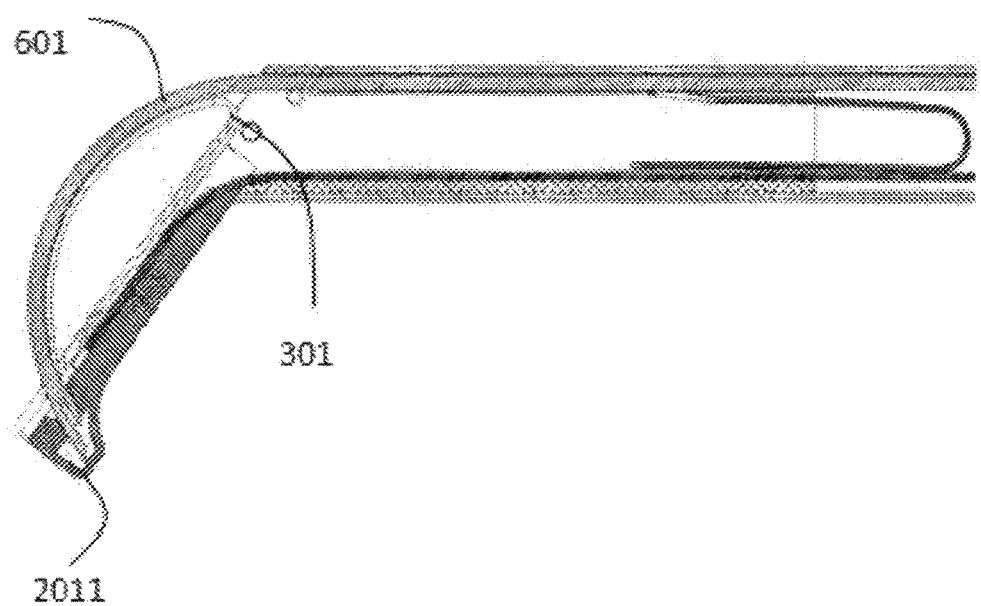

FIG. 24C illustrates the driver member 601 and the receiving end 339 approaching the delivery tip's distal end 2011. The distal end 2011 is shaped as a bowl so that both the driver member 601 (with receiving end 339 engaged therewith) and the opposite end 3055 of the fastener 301 can engage together to form the closed loop.

Figure 24D:
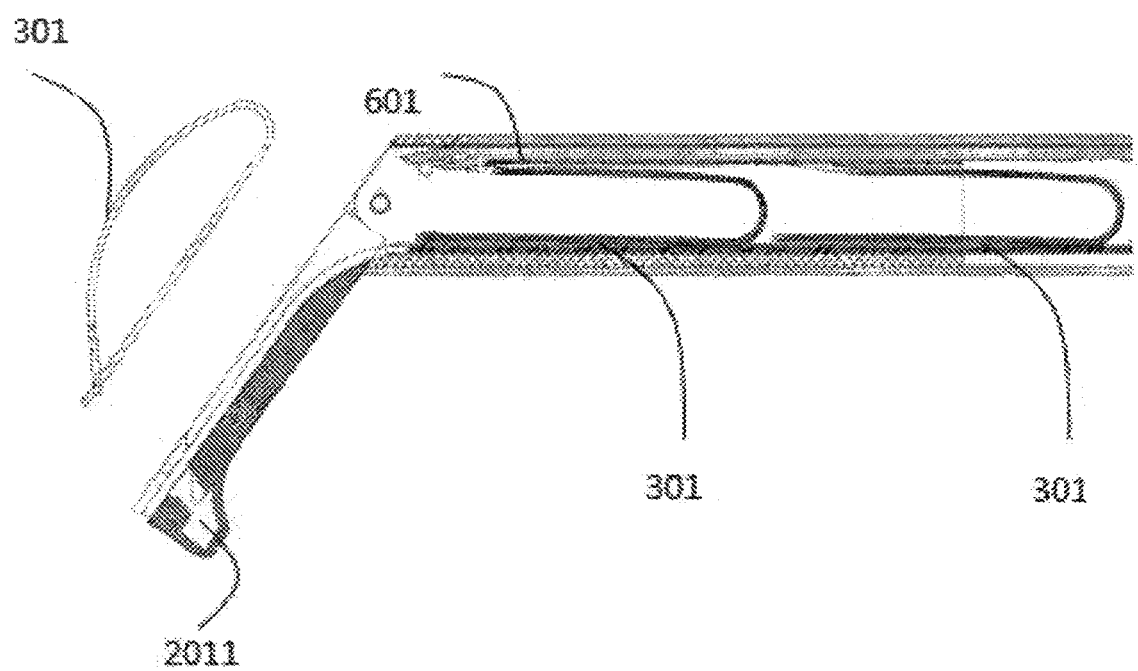

FIG. 24D shows the closed fastener released in tissue 505 and the driver member 601 retracts back into the shaft 103 to engage with a second fastener.

An important feature of the surgical fastening device 1010 is the control over delivery depth and the fastening strength that are afforded by the particular dimensional relationships of the fastener 301 and the device 1010. Placing the tissue-facing surface 207 against tissue and pulling the trigger 117 causes the driver member 601 to push the opposite end 3055 through the tissue and into the receiving end 339 of the fastener back on the outside of the tissue, forming the fastener 301 into the closed loop.

Figure 24E:
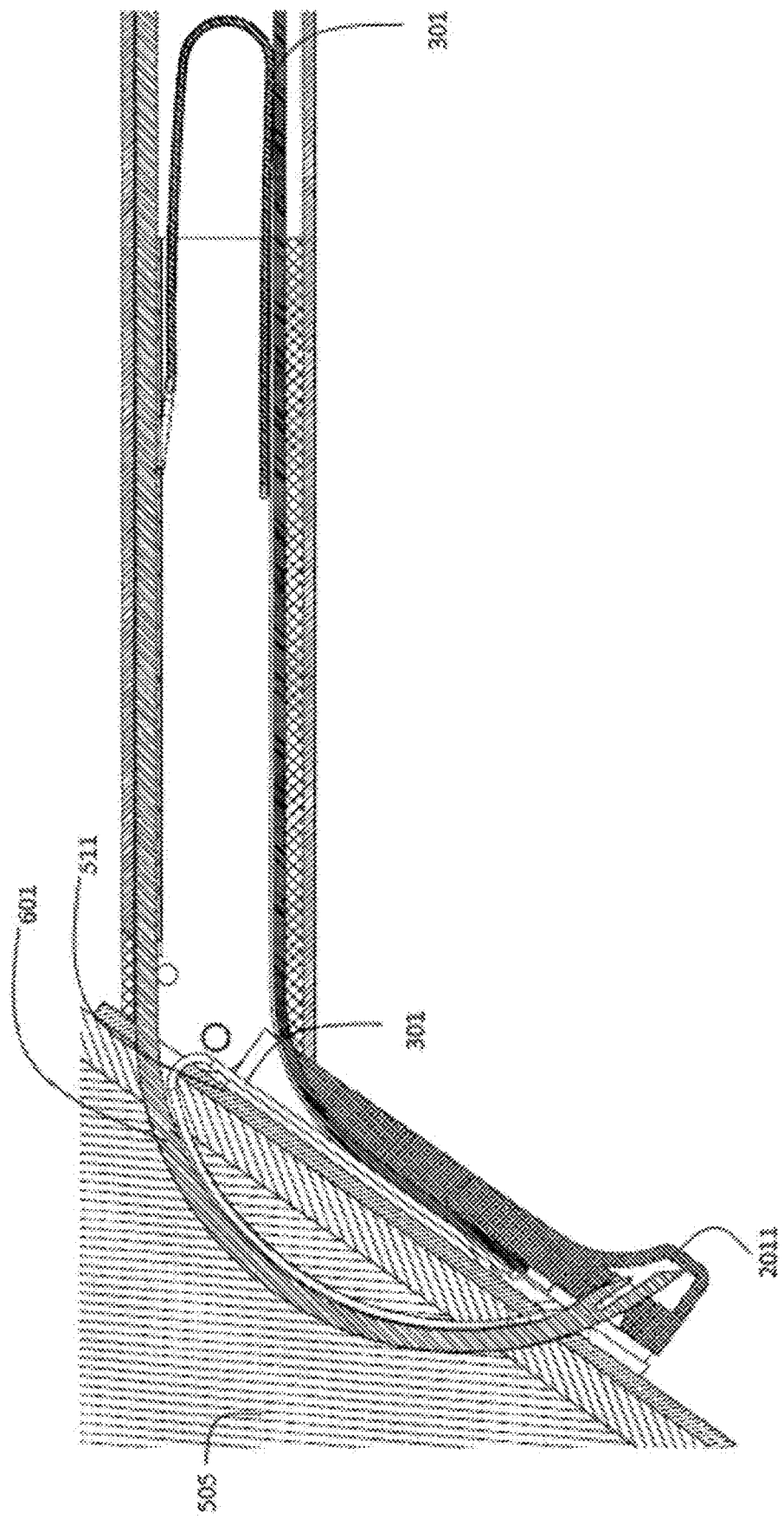

FIG. 24E shows a fastener 301 formed into the closed loop 401 with the delivery tip 201 still in place against tissue 505. Here, the device 1010 has been used to fasten a mesh 511 to the tissue 505. The shaft 103 is positioned such that the tissue-facing surface 207 of the delivery tip 201 faces the mesh 511 and a surface of the tissue 505. The closed fastener 401 spans a width W across a surface of the tissue and penetrates to a depth H within the tissue. Because the delivery tip 201 is biased away from the shaft 103 such that an axis of the shaft 103 and the tissue facing surface 207 form an acute angle, A, the shaft 103 forms the angle A with the surface of the tissue 505. In preferred embodiments, the shaft is dimensioned for minimally-invasive surgery and has a length L of at least 15 cm and has a diameter D of less than 1 cm. More preferably, L>25 cm and D<7 mm Most preferably, H<D<W.

Figure 25A:
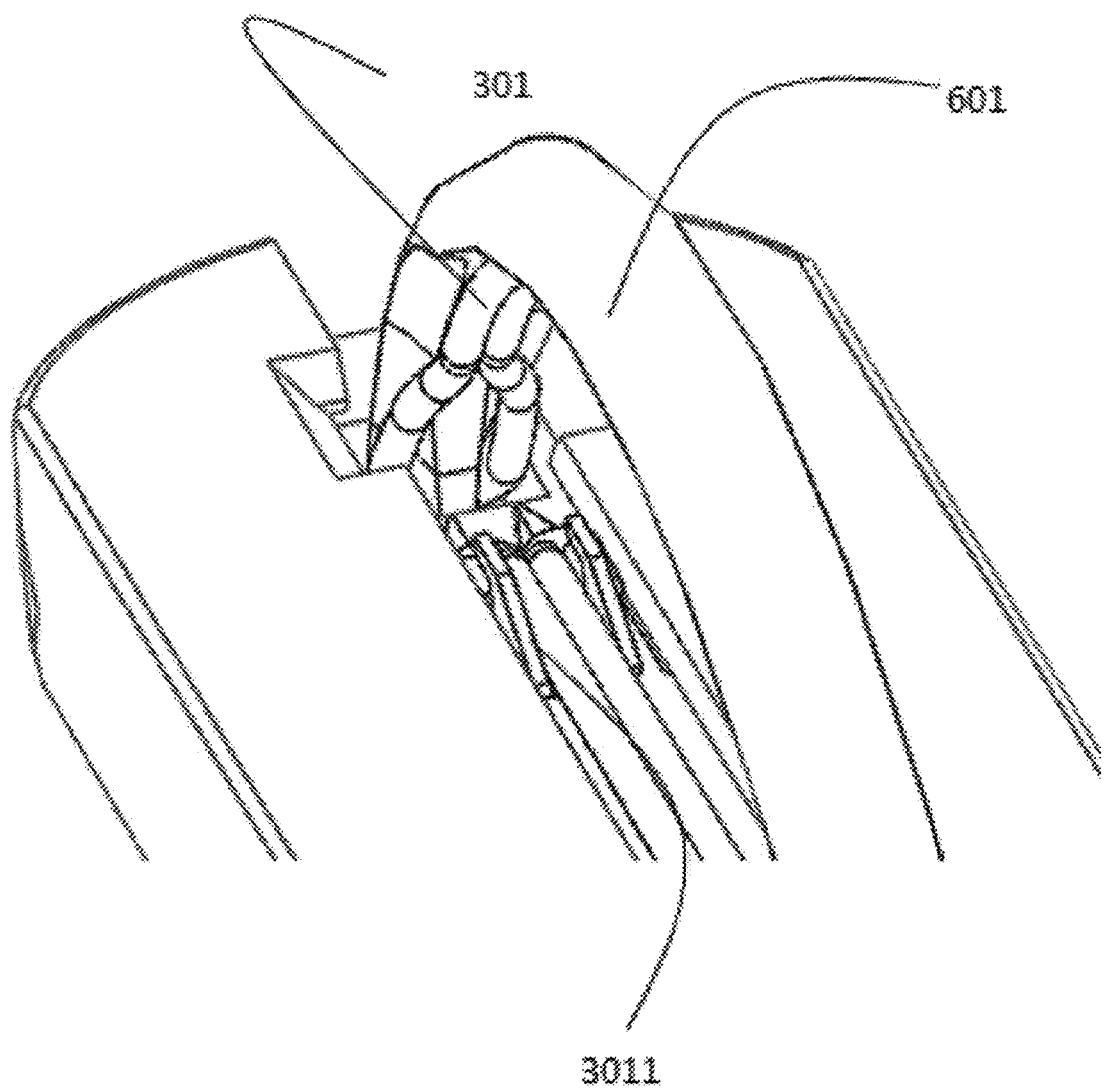
FIGS. 25A-25B show the internal driver 3011.
Figure 25B:
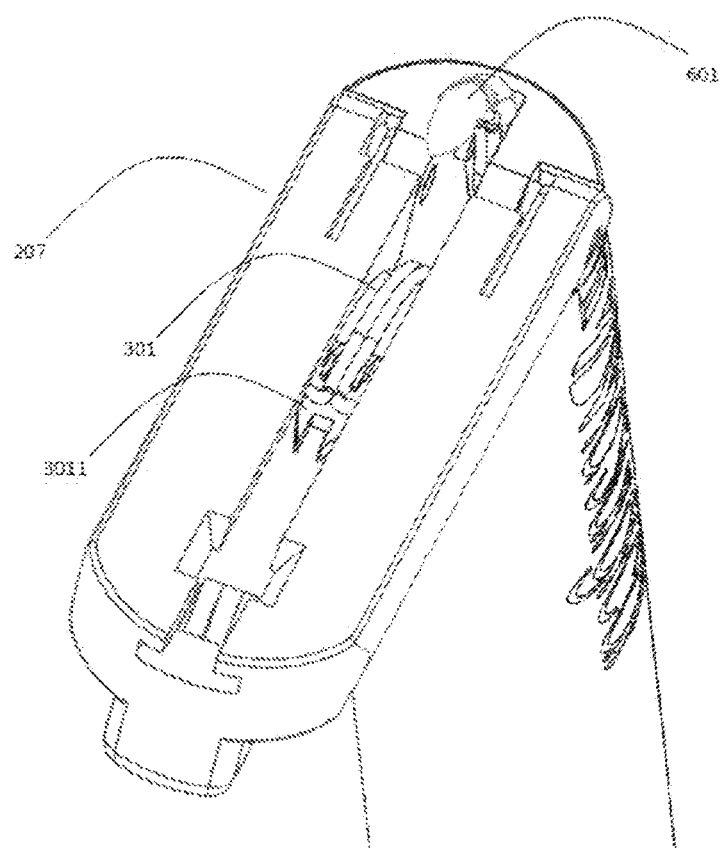

Reference is now made to FIGS. 25A-25B which illustrate another element of this embodiment. According to this embodiment internal driver 3011 is provided within the delivery end 201 and is adapted to promote the opposite end 3055 towards the delivery tip's distal end 2011.

As mentioned above, the distal end 2011 is shaped as a bowl so that both the driver member 601 (with receiving end 339 engaged therewith) and the opposite end 3055 of the fastener 301 can engage together to form the closed loop.

Figure 26:
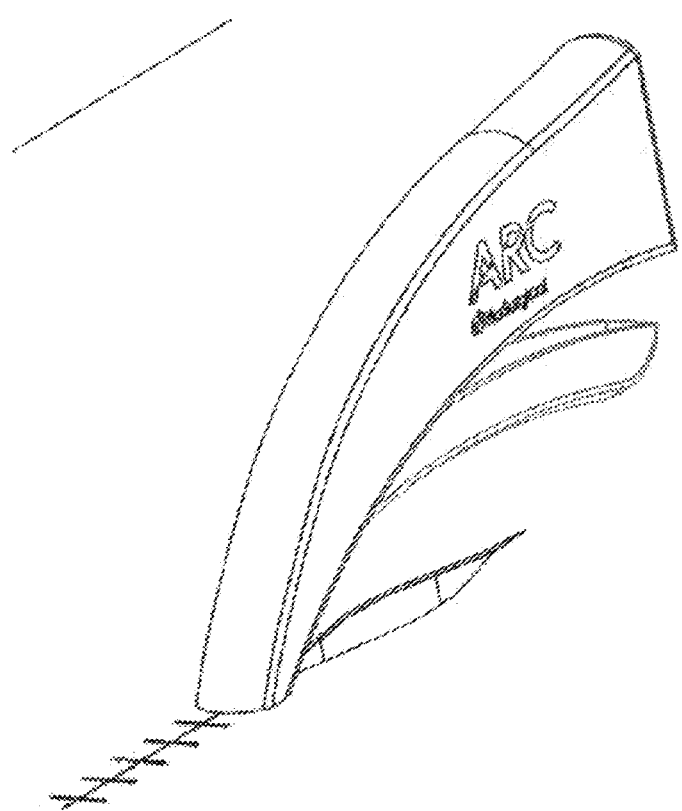
FIG. 26 shows the use of the device as a skin stapler.

Reference is now made to FIG. 26 which illustrates another use of the present invention. The above mentioned surgical fastening device 1010 can be used as a skin stapler.

One of the key main features of devices 101 and 1010 is the ability to introduce a surgical fastening device with the ability to provide sutures of more than the width of the trocar throughout which the device is introduced. For example, the devices 101 and 1010 can provide 10 mm sutures while the trocar being used is a regular 5 mm trocar.

This is enabled by coupling the delivery tip 201 to the shaft 103 by means of 2 hinges and springs, such that the delivery tip 201 is rotatable relatively to the shaft 103.

Figure 27A:
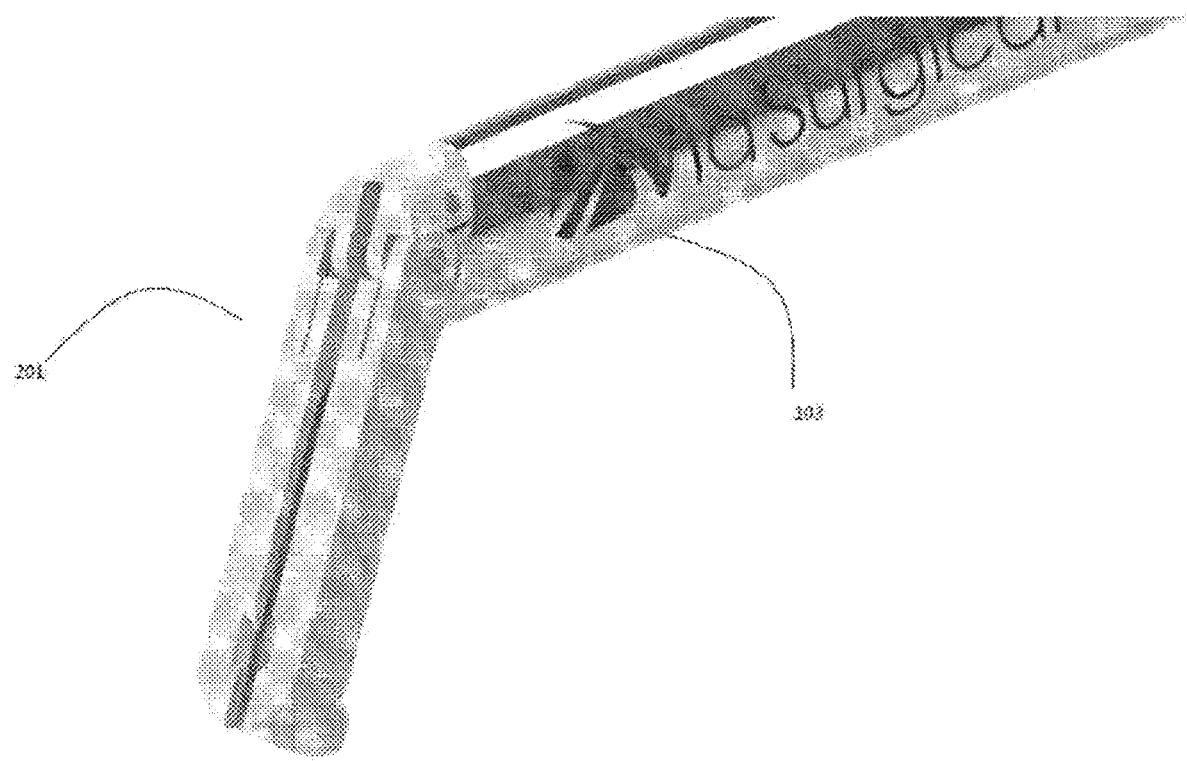
FIG. 27A shows the default configuration in which the delivery tip less than 90 degrees relatively to shaft 103.

According to one embodiment of the present invention, the default configuration of the delivery tip 201 is less than approx. 90 degrees relatively to shaft 103 (see FIG. 27A). More preferably approx. 55 degrees. Most preferably approx. 45 degrees.

Figure 27B:
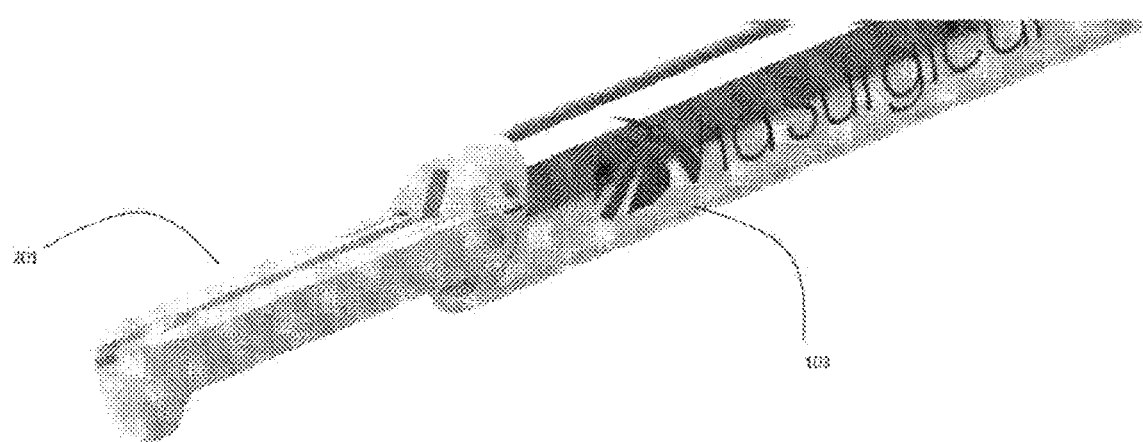
FIG. 27B shows the default configuration in which the delivery tip is aligned with shaft 103.

When external constraining force is applied the delivery tip 201 is aligned with shaft 103 (see FIG. 27B). In that manner, when the device is in the trocar, external constraining force is applied to the delivery tip 201 and thus, it is aligned relatively to shaft 103. When the device exits the trocar, no forces are applied and the delivery tip 201 returns to its default configuration (i.e., less than approx. 90 degrees relatively to shaft 103).

Thus, the either device (101 or 1010) can provide sutures of more than the width of the trocar throughout which the device is introduced.

FIG. 20 shows a surgical fastening device 1011. The device 1011 includes an extended shaft 103 dimensioned for insertion into a surgical site and a delivery tip 201 at the distal end of the shaft.

FIG. 22 is a close-up of the delivery tip 201, showing a driver member 601 disposed within the shaft; and a fastener 301 held at the delivery tip.

FIG. 21A shows the fastener 301 held in a closed configuration, showing that the faster 301 includes an extended body, at least a portion of the extended body being flexibly deformable, the extended body terminating at an engaging end 3055 and a receiving end 339, wherein the receiving end defines a loop with an opening. The engaging end does not include any point or barb. Bending the deformable portion of the extended body and inserting the engaging end into the receiving end locks the fastener in a closed loop. Preferably, the engaging end comprises a wider portion that interlocks with the receiving end. When the fastener is locked in the closed loop, the engaging end is confined by the loop. The closed fastener may include: the wider portion of the engaging end trapped by the loop of the receiving end, a first portion of the extended body extending substantially straight from the loop, a bent portion of the extended body at an end of the first portion, and a bowed portion of the extended body defining a curve between the engaging end and the bent portion. With reference to FIG. 10, the closed loop spans a width W from the barbed end confined within the bowl to the bent portion and the bowed portion is spaced apart from the first portion no greater than a depth H. Preferably, 3 cm>W>H, H<6 mm, or both.

FIG. 21B shows the fastener 301 in an open configuration. The fastener 301 has an extended body 319 with a receiving end 339 and an engaging end 3055. The device 1011 may be characterized in that the engaging end does not have any points or barbs.

FIG. 23A shows that the deliver tip includes a tissue-facing surface.

FIG. 23B shows operating the device 1011 to push, via the driver member 601, the receiving end of the fastener out of the delivery tip.

FIG. 23C shows pushing the receiving end along a path back toward the distal end of delivery tip.

FIG. 23D shows pushing the engaging end towards the distal end of the delivery tip into the receiving end to form the fastener into a closed fastener, and release from the closed fastener, the device. FIGS. 24A-24E also illustrate that the device 1011 is operable to push, via the driver member, the receiving end of the fastener out of the delivery tip, along a path back toward the distal end of delivery tip, push the engaging end towards the distal end of the delivery tip into the receiving end to form the fastener into a closed fastener, and release from the closed fastener, the device characterized in that FIG. 21B, FIG. 21C, FIG. 21D, and FIG. 21E each show embodiments of a fastener in which a receiving end comprises an open loop and the engaging end comprises a wide portion that gets captured by the open loop when the engaging end is pushed into the receiving end.

FIG. 20 shows that the device 1011 may include a body comprising a handle and having a trigger extending therefrom, wherein the extended shaft extends from the body. Optionally, operation of the trigger causes the driver member to retract back into the shaft and engage a second fastener after the closed fastener is released.

Preferably the delivery tip is conformable to more than one position.

FIG. 27A shows the delivery tip of the device 1011 conformed to a default configuration in which the delivery tip is at an angle smaller than 90 degrees relative to the shaft.

FIG. 27B shows that the deliver tip can be conformed to second configuration in which the delivery tip is aligned with said shaft. Preferably, when the device 1011 is in a trocar the delivery tip 201 is held by the trocar in the second configuration illustrated in FIG. 27B and when said device exits said trocar the delivery tip assumes the default configuration shown in FIG. 27A.

FIG. 22 shows that the driver member 601 comprises at least one sharp tip adapted to penetrate the tissue. Preferably, the driver member additionally comprises at least one hook adapted to engage with the receiving end of said fastener, the hook adapted to grasp the receiving end of said fastener, wherein the receiving end of said fastener is enclosed by said hook and said sharp tip of the driver member.

FIG. 10 shows that placing the tissue-facing surface against tissue and operating the device 1011 causes the driver member to push the receiving end through the tissue and to the engaging end of the fastener outside of the tissue such that the closed fastener spans a width W across a surface of the tissue and penetrates to a depth H within the tissue. In some embodiments, the shaft has a length L of at least 15 cm and has a diameter D of less than 1.55 cm. Preferably, L≥25 cm and D≤10 mm Optionally, H<D<W.

References to other documents, such as patents, patent publications, and articles, are made in this disclosure. All such documents are incorporated by reference.

Various modifications of the invention and many further embodiments thereof, in addition to those shown and described herein, will become apparent to those skilled in the art from the full contents of this document, including references to the scientific and patent literature cited herein. The disclosure herein contains information, exemplification and guidance that can be adapted to the practice of this invention in its various embodiments and equivalents thereof.

EXAMPLES

Laparoscopic sacrocolpopexy for pelvic organ prolapse (POP).

Figure 18:
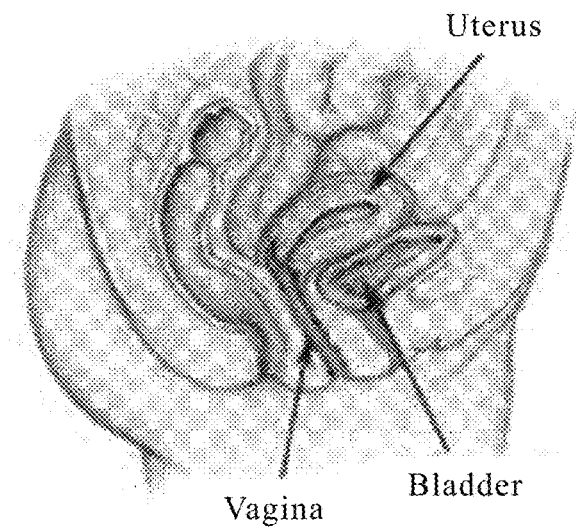
FIG. 18 illustrates pelvic organ prolapse.
Figure 18:
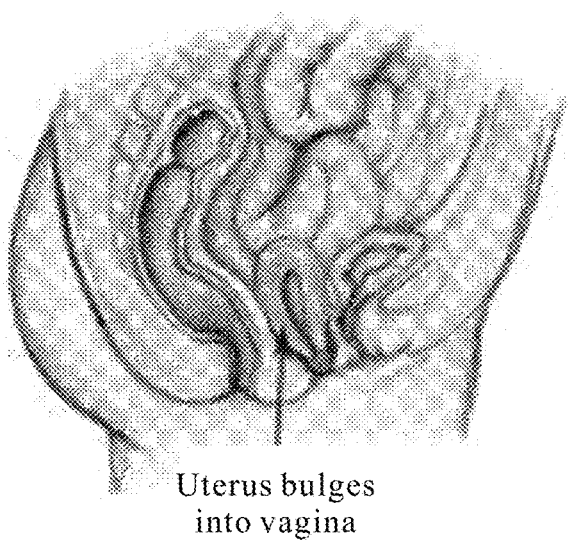

FIG. 18 illustrates pelvic organ prolapse. As reported in Swift, 2000, Am J Obstet Gynecol 183(2):277-85 (incorporated by reference), approximately half of all women older than 50 years complain of symptomatic prolapse.

The health care impact of prolapse is likely to expand, based upon estimates of an increasing prevalence in the growing population of elderly women. See Wu et al., 2009, Forecasting the prevalence of pelvic floor disorders in U.S. Women: 2010 to 2050, Obstet Gynecol 114:1278, incorporated by reference. Surgical repair of prolapse was the most common inpatient procedure performed in women older than 70 years from 1979 to 2006. See Oliphant et al., 2010, Trends over time with commonly performed obstetric and gynecologic inpatient procedures, Obstet Gynecol 116:926, incorporated by reference.

Laparoscopic sacrocolpopexy is a surgical technique for repairing pelvic organ prolapse.

Figure 19:
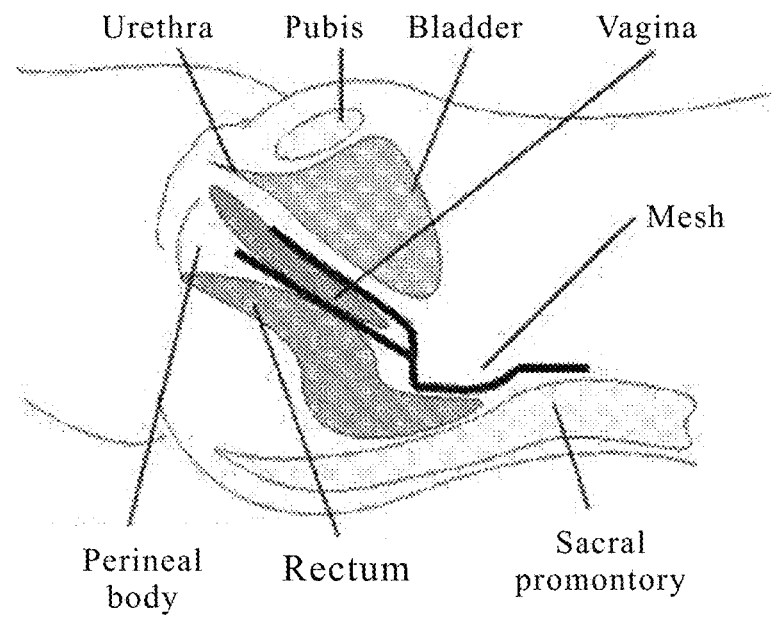
FIG. 19 diagrams a sacrocolpopexy procedure.

FIG. 19 diagrams the sacrocolpopexy procedure. During this procedure a piece of a pre-shaped mesh is inserted into the abdomen and attached to the vaginal wall, then, the other end of the mesh is attached to the back portion of the pelvic (sacral promontory) therefore, lifting the vagina and preventing the prolapse. Attachment of the mesh to the vagina wall by suturing is challenging because it require the insertion of the suture to a specific depth into the vaginal wall. The suture must provide a secure attachment, but should not pass through the vagina wall since that may cause serious complications.

The mesh may be attached using a method of attaching a mesh according to this disclosure. The method includes obtaining a surgical fastening device that includes a body with a handle with a trigger extending therefrom; a shaft extending from the body; a delivery tip at a distal end of the shaft; a driver member disposed within the shaft; and a fastener held at the delivery tip. The fastener has an extended body with a barbed end and a receiving end.

The method includes operating the trigger to cause the driver member to: push the barbed end of the fastener out of the delivery tip, along a curved path, and into the receiving end, thereby forming the fastener into a closed fastener; release from the closed fastener; and retract back into the shaft and engage a second fastener. Preferably, the delivery tip protrudes from the shaft and presents a tissue-facing surface that presents an exit port. The fastener is held at the delivery tip at least partially within a guide slot. In preferred embodiments of the method, the delivery tip is biased away from the shaft such that an axis of the shaft and the tissue-facing surface form an acute angle and the driver member comprises a shape-memory material that biases the driver member into a curved shape.

The method includes constraining the driver member in a straight shape by having the driver member disposed within the shaft within a delivery slot.

Preferably, the barbed end of the fastener comprises one or more barbs and a pushable surface engaged with a distal tip of the driver member and the receiving end of the fastener defines a bowl with an opening and a lip that overhangs the opening. It may be that the exit port encompasses an end of the delivery slot.

The method may include operating the trigger to cause the driver member to: push the barbed end of the fastener out of the distal end of the delivery slot, along a curved path to the distal end of the guide slot, and into the receiving end of the fastener such that the one or more barbs are engaged with the lip of the bowl of receiving end, thereby forming the fastener into a closed fastener.

Preferably, the method also includes placing the tissue-facing surface against tissue and pulling the trigger, causing the driver member to push the barbed end through the tissue and into the receiving end of the fastener outside of the tissue such that the closed fastener spans a width W across a surface of the tissue and penetrates to a depth H within the tissue. The shaft may have a length L of at least 15 cm and has a diameter D of less than 1 cm. In preferred embodiments of the method, L≥25 cm and D≤7 mm. Also, H<D<W.

The method may include bending the delivery tip towards the axis of the shaft (e.g., for insertion through a standard trocar or incision during minimally-invasive surgery). Method may include delivering one or more additional fasteners from the shaft, by operating the trigger to deliver a single fastener and advance any remaining fasteners towards the delivery tip.

What is claimed is:

1. A surgical fastening device comprising:
a shaft comprising a proximal portion and a distal end;
a delivery tip at the distal end of the shaft;
a fastener held at the delivery tip, the fastener having an extended body with a receiving end and an opposite end; and a driver member disposed within the shaft, having a sharp tip adapted to penetrate a tissue, and a hook;

wherein the driver member is operable to:

extend to engage the receiving end of the fastener with the hook, enclosing the receiving end between the sharp tip and the hook, and move the receiving end of the fastener out of the delivery tip, along a curved path toward a distal end of the delivery tip.

2. The surgical fastening device of claim 1, wherein the receiving end comprises a loop, and the hook engages with the receiving end by insertion into the loop.

3. The surgical fastening device of claim 2, wherein the sharp tip remains outside of the loop when the receiving end is enclosed between the sharp tip and the hook.

4. The surgical fastening device of claim 1, comprising an internal driver within the delivery tip, configured to promote the opposite end of the fastener toward the distal end of the delivery tip where it is received by the opposite end of the fastener.

5. The surgical fastening device of claim 1, wherein the driver member holds the receiving end in a portion of the distal end of the delivery tip shaped as a bowl while the receiving end receives the opposite end of the fastener.

6. The surgical fastening device of claim 5, wherein the curved path forms a portion of the extended body of the fastener into a bowed portion, spaced away from a straight first portion of the extended body.

7. The surgical fastening device of claim 6, wherein the curved path is spaced away from the extended body by a distance less than 6 mm.

8. The surgical fastening device of claim 6, wherein the driver member extends along a whole side of the receiving end of the fastener opposite the delivery tip.

9. The surgical fastening device of claim 1, wherein the path toward the distal end of the delivery tip is a curved path.

10. The surgical fastening device of claim 1, wherein the opposite end is barbed.

11. The surgical fastening device of claim 1, wherein the fastener is made of at least one piece of a monofilament suture or a multifilament suture.

12. The surgical fastening device of claim 1, wherein the driver member is further operable to:

hold the receiving end at the distal end of the delivery tip while the receiving end receives the opposite end of the fastener, forming the fastener into a closed fastener, and release from the closed fastener.

13. The surgical fastening device of claim 1, wherein the delivery tip is coupled to the shaft through a hinge and spring arrangement.

14. The surgical fastening device of claim 13, wherein the hinge and spring arrangement comprises two hinges and a plurality of springs.

15. The surgical fastening device of claim 13, wherein the delivery tip rotates relative to the shaft around an axis defined by the hinge and spring arrangement.

16. The surgical fastening device of claim 1, wherein the delivery tip rotates relative to the shaft while remaining straight, from a confined position aligned with the shaft to an unconfined position unaligned with the shaft, and at an angle of less than 90° relative to the shaft.

17. The surgical fastening device of claim 1, wherein the driver member has a proximal side and a distal side terminating in the sharp tip, and a distal tip of the hook is located proximal to the sharp tip.

18. The surgical fastening device of claim 1, wherein the hook extends distally along the driver member from a location of attachment to the driver member.

19. The surgical fastening device of claim 1, wherein the driver member has a proximal side and a distal side terminating in the sharp tip, and the sharp tip broadens in a proximal direction to be wider than the receiving end and the hook.

20. The surgical fastening device of claim 1, wherein the sharp tip and the hook define a slot between them in which the receiving end of the fastener is enclosed.

* * * * *

UNITED STATES PATENT AND TRADEMARK OFFICE
CERTIFICATE OF CORRECTION

| | | |
|---|---|---|
| PATENT NO. | : 12,029,411 B2 | |
| APPLICATION NO. | : 17/420693 | |
| DATED | : July 9, 2024 | |
| INVENTOR(S) | : Ofek Levin, Arie Levy and Lena Levin | |

It is certified that error appears in the above-identified patent and that said Letters Patent is hereby corrected as shown below:

On the Title Page

Item (73), Assignee, "CATCHER TECHNOLOGY., LTD." should read --CATCHER TECHNOLOGY CO., LTD.--

Signed and Sealed this
Sixth Day of August, 2024

Katherine Kelly Vidal
*Director of the United States Patent and Trademark Office*